US010881343B2

(12) United States Patent
Bullington et al.

(10) Patent No.: US 10,881,343 B2
(45) Date of Patent: *Jan. 5, 2021

(54) FLUID DIVERSION MECHANISM FOR BODILY-FLUID SAMPLING

(71) Applicant: Magnolia Medical Technologies, Inc., Seattle, WA (US)

(72) Inventors: Gregory J. Bullington, Bellevue, WA (US); Richard G. Patton, Seattle, WA (US); Jay M. Miazga, Seattle, WA (US); Shan E. Gaw, Seattle, WA (US)

(73) Assignee: Magnolia Medical Technologies, Inc., Seattle, WA (US)

( * ) Notice: Subject to any disclaimer, the term of this patent is extended or adjusted under 35 U.S.C. 154(b) by 587 days.

This patent is subject to a terminal disclaimer.

(21) Appl. No.: 14/926,784

(22) Filed: Oct. 29, 2015

(65) Prior Publication Data
US 2016/0113560 A1   Apr. 28, 2016

Related U.S. Application Data

(63) Continuation of application No. 13/952,964, filed on Jul. 29, 2013, now Pat. No. 9,204,864.
(Continued)

(51) Int. Cl.
*A61B 5/153*   (2006.01)
*A61B 5/154*   (2006.01)
(Continued)

(52) U.S. Cl.
CPC .... *A61B 5/150221* (2013.01); *A61B 5/15003* (2013.01); *A61B 5/153* (2013.01);
(Continued)

(58) Field of Classification Search
CPC .......... A61B 5/150221; A61B 5/15003; A61B 5/150992; A61B 5/154; A61B 5/1545;
(Continued)

(56) References Cited

U.S. PATENT DOCUMENTS 2,707,953 A   5/1955   Ryan
2,992,974 A   7/1961   Belcove et al.
(Continued)

FOREIGN PATENT DOCUMENTS

CN   2907683 Y   6/2007
CN   101060871 A   10/2007
(Continued)

OTHER PUBLICATIONS

Office Action for U.S. Appl. No. 14/498,102, dated Oct. 17, 2017, 21 pages.
(Continued)

*Primary Examiner* — David J. McCrosky
(74) *Attorney, Agent, or Firm* — Cooley LLP

(57) ABSTRACT

A device includes a pre-sample reservoir, an actuator mechanism, and a diverter. The pre-sample reservoir can be fluidically coupled to a delivery member to receive and isolate a predetermined volume of bodily-fluid withdrawn from a patient. The actuator mechanism is operably coupled to the pre-sample reservoir such that, when actuated, a negative pressure is formed in the pre-sample reservoir that urges the bodily-fluid to flow into the pre-sample reservoir. The diverter can selectively control fluid flow between the delivery member and the pre-sample reservoir. The diverter includes a flow control mechanism that defines a first fluid flow path and a second fluid flow path. The diverter is movable between a first configuration in which the bodily-fluid flows through the first fluid flow path to the pre-sample reservoir, and a second configuration in which the bodily-fluid flows through the second fluid flow path to a sample reservoir coupled to the diverter.

19 Claims, 15 Drawing Sheets

Related U.S. Application Data

(60) Provisional application No. 61/678,404, filed on Aug. 1, 2012.

(51) Int. Cl.
 *A61B 10/00* (2006.01)
 *A61B 5/15* (2006.01)

(52) U.S. Cl.
 CPC .. *A61B 5/150099* (2013.01); *A61B 5/150916* (2013.01); *A61B 10/0045* (2013.01); *A61B 10/0096* (2013.01); *A61B 5/154* (2013.01); *A61B 5/150236* (2013.01); *A61B 5/150244* (2013.01)

(58) Field of Classification Search
 CPC ........ A61B 5/150213; A61B 5/150473; A61B 5/1438; A61B 5/150343; A61B 5/150229; A61B 5/150244; A61B 5/150206; A61B 5/150267; A61B 5/150488; A61B 5/150496; A61B 5/150946; A61B 5/150251; A61B 5/150099
 See application file for complete search history.

(56) References Cited

U.S. PATENT DOCUMENTS

| | | | |
|---|---|---|---|
| 3,013,557 | A | 12/1961 | Pallotta |
| 3,098,016 | A | 7/1963 | Cooper et al. |
| 3,382,865 | A | 5/1968 | Worral, Jr. |
| 3,405,706 | A | 10/1968 | Cinqualbre |
| 3,467,095 | A * | 9/1969 | Ross .................. A61M 1/3672 422/44 |
| 3,494,351 | A | 2/1970 | Horn |
| 3,494,352 | A | 2/1970 | Russo et al. |
| 3,577,980 | A | 5/1971 | Cohen |
| 3,604,410 | A | 9/1971 | Whitacre |
| 3,635,798 | A | 1/1972 | Kirkham et al. |
| 3,648,684 | A | 3/1972 | Barnwell et al. |
| 3,741,197 | A | 6/1973 | Sanz et al. |
| 3,777,773 | A | 12/1973 | Tolbert |
| 3,817,240 | A | 6/1974 | Ayres |
| 3,834,372 | A | 9/1974 | Turney |
| 3,835,835 | A | 9/1974 | Thompson et al. |
| 3,848,579 | A | 11/1974 | Villa-Real |
| 3,848,581 | A | 11/1974 | Cinqualbre et al. |
| 3,874,367 | A | 4/1975 | Ayres |
| 3,886,930 | A | 6/1975 | Ryan |
| 3,890,203 | A | 6/1975 | Mehl |
| 3,890,968 | A | 6/1975 | Pierce et al. |
| 3,937,211 | A | 2/1976 | Merten |
| 3,945,380 | A | 5/1976 | Dabney et al. |
| 3,978,846 | A | 9/1976 | Bailey |
| 4,056,101 | A | 11/1977 | Geissler et al. |
| 4,057,050 | A | 11/1977 | Sarstedt |
| 4,063,460 | A | 12/1977 | Svensson |
| 4,077,395 | A | 3/1978 | Woolner |
| 4,106,497 | A | 8/1978 | Percarpio |
| 4,133,863 | A | 1/1979 | Koenig |
| 4,150,089 | A | 4/1979 | Linet |
| 4,154,229 | A | 5/1979 | Nugent |
| 4,166,450 | A | 9/1979 | Abramson |
| 4,193,400 | A | 3/1980 | Loveless et al. |
| 4,207,870 | A | 6/1980 | Eldridge |
| 4,212,308 | A | 7/1980 | Percarpio |
| 4,257,416 | A | 3/1981 | Prager |
| 4,275,730 | A | 6/1981 | Hussein |
| 4,340,067 | A | 7/1982 | Rattenborg |
| 4,340,068 | A | 7/1982 | Kaufman |
| 4,349,035 | A | 9/1982 | Thomas et al. |
| 4,370,987 | A | 2/1983 | Bazell et al. |
| 4,398,544 | A | 8/1983 | Nugent et al. |
| 4,412,548 | A | 11/1983 | Hoch |
| 4,416,290 | A | 11/1983 | Lutkowski |
| 4,425,235 | A | 1/1984 | Cornell et al. |
| 4,444,203 | A | 4/1984 | Engelman |
| 4,459,997 | A | 7/1984 | Sarstedt |
| 4,509,534 | A | 4/1985 | Tassin, Jr. |
| 4,537,593 | A | 8/1985 | Alchas |
| 4,608,996 | A | 9/1986 | Brown |
| 4,654,027 | A * | 3/1987 | Dragan ........... A61M 25/10185 137/614.2 |
| 4,657,027 | A | 4/1987 | Paulsen |
| 4,657,160 | A | 4/1987 | Woods et al. |
| 4,673,386 | A | 6/1987 | Gordon |
| 4,676,256 | A | 6/1987 | Golden |
| 4,679,571 | A | 7/1987 | Frankel et al. |
| 4,705,497 | A | 10/1987 | Shitaokoshi et al. |
| 4,714,461 | A | 12/1987 | Gabel |
| 4,737,146 | A | 4/1988 | Amaki et al. |
| 4,772,273 | A | 9/1988 | Alchas |
| 4,790,830 | A | 12/1988 | Hamacher |
| 4,808,157 | A | 2/1989 | Coombs |
| 4,865,583 | A | 9/1989 | Tu |
| 4,886,072 | A | 12/1989 | Percarpio et al. |
| 4,890,627 | A | 1/1990 | Haber et al. |
| 4,904,240 | A | 2/1990 | Hoover |
| 4,988,339 | A | 1/1991 | Vadher |
| 5,009,847 | A | 4/1991 | Solomons |
| 5,027,827 | A | 7/1991 | Cody et al. |
| 5,032,116 | A | 7/1991 | Peterson et al. |
| 5,045,185 | A | 9/1991 | Ohnaka et al. |
| 5,066,284 | A | 11/1991 | Mersch et al. |
| 5,084,034 | A | 1/1992 | Zanotti |
| 5,097,842 | A * | 3/1992 | Bonn ............... A61B 5/150038 600/575 |
| 5,100,390 | A | 3/1992 | Lubeck et al. |
| 5,100,394 | A | 3/1992 | Dudar et al. |
| 5,108,927 | A | 4/1992 | Dom |
| 5,116,323 | A | 5/1992 | Kreuzer et al. |
| 5,122,129 | A | 6/1992 | Olson et al. |
| 5,135,489 | A | 8/1992 | Jepson et al. |
| 5,222,502 | A | 6/1993 | Kurose |
| 5,234,406 | A | 8/1993 | Drasner et al. |
| 5,269,317 | A | 12/1993 | Bennett |
| 5,330,464 | A | 7/1994 | Mathias et al. |
| 5,417,673 | A | 5/1995 | Gordon |
| 5,429,610 | A | 7/1995 | Vaillancourt |
| 5,431,811 | A | 7/1995 | Tusini et al. |
| 5,439,450 | A | 8/1995 | Haedt |
| 5,449,351 | A | 9/1995 | Zohmann |
| 5,450,856 | A | 9/1995 | Norris |
| 5,454,786 | A | 10/1995 | Harris |
| 5,466,228 | A | 11/1995 | Evans |
| 5,485,854 | A | 1/1996 | Hollister |
| 5,507,299 | A | 4/1996 | Roland |
| 5,520,193 | A | 5/1996 | Suzuki et al. |
| 5,573,510 | A | 11/1996 | Isaacson |
| 5,575,777 | A | 11/1996 | Cover et al. |
| 5,577,513 | A | 11/1996 | Van Vlassalaer |
| 5,603,700 | A | 2/1997 | Daneshvar |
| 5,628,734 | A | 5/1997 | Hatfalvi |
| 5,632,906 | A | 5/1997 | Ishida et al. |
| 5,649,912 | A | 7/1997 | Peterson |
| 5,691,486 | A | 11/1997 | Behringer et al. |
| 5,718,678 | A | 2/1998 | Fleming, III |
| 5,749,857 | A | 5/1998 | Cuppy |
| 5,762,633 | A | 6/1998 | Whisson |
| 5,772,608 | A | 6/1998 | Dhas |
| 5,811,658 | A | 9/1998 | Van Driel et al. |
| 5,824,001 | A | 10/1998 | Erskine |
| 5,848,996 | A | 12/1998 | Eldor |
| 5,857,983 | A | 1/1999 | Douglas et al. |
| 5,865,812 | A | 2/1999 | Correia |
| 5,871,699 | A | 2/1999 | Ruggeri |
| 5,911,705 | A | 6/1999 | Howell |
| 5,922,551 | A | 7/1999 | Durbin et al. |
| 5,961,472 | A | 10/1999 | Swendson et al. |
| 5,971,956 | A | 10/1999 | Epstein |
| 5,980,830 | A | 11/1999 | Savage et al. |
| 6,016,712 | A | 1/2000 | Warden et al. |
| 6,057,105 | A | 5/2000 | Hoon et al. |
| 6,106,509 | A | 8/2000 | Loubser |
| 6,210,909 | B1 | 4/2001 | Guirguis |

(56) References Cited

U.S. PATENT DOCUMENTS

| | | | |
|---|---|---|---|
| 6,224,561 B1 | 5/2001 | Swendson et al. | |
| 6,328,726 B1 | 12/2001 | Ishida et al. | |
| 6,364,847 B1 * | 4/2002 | Shulze | A61B 5/15003 |
| | | | 600/573 |
| 6,364,890 B1 | 4/2002 | Lum et al. | |
| 6,387,086 B2 | 5/2002 | Mathias et al. | |
| 6,403,381 B1 | 6/2002 | Mann et al. | |
| 6,506,182 B2 | 1/2003 | Estabrook et al. | |
| 6,520,948 B1 | 2/2003 | Mathias et al. | |
| 6,569,117 B1 | 5/2003 | Ziv et al. | |
| 6,626,884 B1 | 9/2003 | Dillon et al. | |
| 6,638,252 B2 | 10/2003 | Moulton et al. | |
| 6,648,835 B1 | 11/2003 | Shemesh | |
| 6,692,479 B2 | 2/2004 | Kraus et al. | |
| 6,695,004 B1 | 2/2004 | Raybuck | |
| 6,733,433 B1 | 5/2004 | Fell | |
| 6,736,783 B2 | 5/2004 | Blake et al. | |
| 6,746,420 B1 | 6/2004 | Prestidge et al. | |
| 6,843,775 B2 | 1/2005 | Hyun | |
| 6,860,871 B2 | 3/2005 | Kuracina et al. | |
| 6,905,483 B2 | 6/2005 | Newby et al. | |
| 6,913,580 B2 | 7/2005 | Stone | |
| 6,945,948 B2 | 9/2005 | Bainbridge et al. | |
| 7,025,751 B2 | 4/2006 | Silva et al. | |
| 7,044,941 B2 | 5/2006 | Mathias et al. | |
| 7,052,603 B2 | 5/2006 | Schick | |
| 7,055,401 B2 | 6/2006 | Prybella et al. | |
| 7,087,047 B2 | 8/2006 | Kraus et al. | |
| 7,204,828 B2 | 4/2007 | Rosiello | |
| 7,241,281 B2 | 7/2007 | Coelho et al. | |
| 7,306,736 B2 | 12/2007 | Collins et al. | |
| 7,335,188 B2 | 2/2008 | Graf | |
| 7,384,416 B2 | 6/2008 | Goudaliez et al. | |
| 7,461,671 B2 | 12/2008 | Ehwald et al. | |
| 7,479,131 B2 | 1/2009 | Mathias et al. | |
| 7,614,857 B2 | 11/2009 | Fuechslin et al. | |
| 7,615,033 B2 | 11/2009 | Leong | |
| 7,648,491 B2 | 1/2010 | Rogers | |
| 7,666,166 B1 | 2/2010 | Emmert et al. | |
| 7,744,573 B2 | 6/2010 | Gordon et al. | |
| 7,766,879 B2 | 8/2010 | Tan et al. | |
| 7,993,310 B2 | 8/2011 | Rosiello | |
| 8,070,725 B2 | 12/2011 | Christensen | |
| 8,197,420 B2 | 6/2012 | Patton | |
| 8,231,546 B2 | 7/2012 | Patton | |
| 8,292,841 B2 | 10/2012 | Gregersen | |
| 8,337,418 B2 | 12/2012 | Patton | |
| 8,349,254 B2 | 1/2013 | Hoshino et al. | |
| 8,377,040 B2 | 2/2013 | Burkholz et al. | |
| 8,383,044 B2 | 2/2013 | Davis et al. | |
| 8,412,300 B2 | 4/2013 | Sonderegger | |
| 8,523,826 B2 | 9/2013 | Layton, Jr. | |
| 8,535,241 B2 | 9/2013 | Bullington et al. | |
| 8,540,663 B2 | 9/2013 | Davey et al. | |
| 8,568,371 B2 | 10/2013 | Siopes et al. | |
| 8,574,203 B2 | 11/2013 | Stout et al. | |
| 8,603,009 B2 | 12/2013 | Tan et al. | |
| 8,647,286 B2 | 2/2014 | Patton | |
| 8,795,198 B2 | 8/2014 | Tan et al. | |
| 8,827,958 B2 | 9/2014 | Bierman et al. | |
| 8,864,684 B2 | 10/2014 | Bullington et al. | |
| 8,876,734 B2 | 11/2014 | Patton | |
| 9,022,950 B2 | 5/2015 | Bullington et al. | |
| 9,022,951 B2 | 5/2015 | Bullington et al. | |
| 9,060,725 B2 | 6/2015 | Bullington et al. | |
| 9,138,572 B2 | 9/2015 | Zeytoonian et al. | |
| 9,149,576 B2 | 10/2015 | Bullington et al. | |
| 9,204,864 B2 | 12/2015 | Bullington et al. | |
| 9,314,201 B2 | 4/2016 | Burkholz et al. | |
| 9,855,001 B2 | 1/2018 | Patton | |
| 9,855,002 B2 | 1/2018 | Patton | |
| 9,855,386 B2 | 1/2018 | Close et al. | |
| 9,861,306 B2 | 1/2018 | Patton | |
| 9,872,645 B2 | 1/2018 | Patton | |
| 9,895,092 B2 | 2/2018 | Burkholz | |
| 9,931,466 B2 | 4/2018 | Bullington et al. | |
| 9,950,084 B2 | 4/2018 | Bullington et al. | |
| 10,028,687 B2 | 7/2018 | Patton | |
| 10,028,688 B2 | 7/2018 | Patton | |
| 10,028,689 B2 | 7/2018 | Patton | |
| 10,039,483 B2 | 8/2018 | Bullington et al. | |
| 10,045,724 B2 | 8/2018 | Patton | |
| 10,052,053 B2 | 8/2018 | Patton | |
| 10,220,139 B2 | 3/2019 | Bullington et al. | |
| 10,251,590 B2 | 4/2019 | Bullington et al. | |
| 10,292,633 B2 | 5/2019 | Bullington et al. | |
| 10,299,713 B2 | 5/2019 | Patton | |
| 2002/0002349 A1 | 1/2002 | Flaherty et al. | |
| 2002/0004647 A1 | 1/2002 | Leong | |
| 2002/0107469 A1 | 8/2002 | Bolan et al. | |
| 2002/0183651 A1 | 12/2002 | Hyun | |
| 2002/0193751 A1 | 12/2002 | Theeuwes et al. | |
| 2003/0013991 A1 | 1/2003 | Stone | |
| 2003/0055381 A1 | 3/2003 | Wilkinson | |
| 2003/0069543 A1 | 4/2003 | Carpenter et al. | |
| 2003/0105414 A1 | 6/2003 | Leong | |
| 2003/0208151 A1 * | 11/2003 | Kraus | A61B 5/412 |
| | | | 604/4.01 |
| 2004/0009542 A1 | 1/2004 | Dumont et al. | |
| 2004/0010228 A1 | 1/2004 | Swenson et al. | |
| 2004/0054283 A1 | 3/2004 | Corey et al. | |
| 2004/0054333 A1 | 3/2004 | Theeuwes et al. | |
| 2004/0127816 A1 | 7/2004 | Galvao | |
| 2004/0147855 A1 | 7/2004 | Marsden | |
| 2005/0004524 A1 | 1/2005 | Newby et al. | |
| 2005/0148993 A1 | 7/2005 | Mathias et al. | |
| 2005/0161112 A1 | 7/2005 | Ehwald et al. | |
| 2005/0199077 A1 | 9/2005 | Prybella et al. | |
| 2005/0240161 A1 | 10/2005 | Crawford | |
| 2005/0245885 A1 | 11/2005 | Brown | |
| 2005/0273019 A1 | 12/2005 | Conway et al. | |
| 2005/0281713 A1 | 12/2005 | Hampsch et al. | |
| 2006/0251622 A1 | 11/2006 | Suzuki et al. | |
| 2006/0287639 A1 | 12/2006 | Sharp | |
| 2007/0088279 A1 | 4/2007 | Shue et al. | |
| 2007/0100250 A1 | 5/2007 | Kline | |
| 2007/0119508 A1 | 5/2007 | West et al. | |
| 2007/0287948 A1 | 12/2007 | Sakiewicz | |
| 2008/0108954 A1 | 5/2008 | Mathias et al. | |
| 2008/0145933 A1 | 6/2008 | Patton | |
| 2008/0167577 A1 | 7/2008 | Weilbacher et al. | |
| 2008/0185056 A1 | 8/2008 | Diodati et al. | |
| 2008/0319346 A1 | 12/2008 | Crawford et al. | |
| 2009/0050213 A1 | 2/2009 | Biddell et al. | |
| 2009/0227896 A1 | 9/2009 | Alvin Tan et al. | |
| 2009/0306601 A1 | 12/2009 | Shaw et al. | |
| 2010/0010372 A1 | 1/2010 | Brown et al. | |
| 2010/0042048 A1 | 2/2010 | Christensen | |
| 2010/0057004 A1 | 3/2010 | Christensen et al. | |
| 2010/0094171 A1 | 4/2010 | Conway et al. | |
| 2010/0152681 A1 | 6/2010 | Mathias | |
| 2010/0234768 A1 | 9/2010 | Uchiyama et al. | |
| 2010/0268118 A1 | 10/2010 | Schweiger | |
| 2011/0306899 A1 | 12/2011 | Brown et al. | |
| 2012/0035540 A1 | 2/2012 | Ferren et al. | |
| 2012/0095367 A1 | 4/2012 | Patton | |
| 2012/0215131 A1 | 8/2012 | Patton | |
| 2012/0265099 A1 | 10/2012 | Goodnow, II et al. | |
| 2013/0079604 A1 | 3/2013 | Patton | |
| 2013/0116599 A1 | 5/2013 | Bullington et al. | |
| 2013/0317391 A1 | 11/2013 | Bullington et al. | |
| 2014/0039348 A1 | 2/2014 | Bullington et al. | |
| 2014/0066880 A1 | 3/2014 | Prince et al. | |
| 2014/0081172 A1 | 3/2014 | Patton | |
| 2014/0107564 A1 | 4/2014 | Bullington et al. | |
| 2014/0155781 A1 | 6/2014 | Bullington et al. | |
| 2014/0155782 A1 | 6/2014 | Bullington et al. | |
| 2015/0011910 A1 | 1/2015 | Bullington et al. | |
| 2015/0011911 A1 | 1/2015 | Bullington et al. | |
| 2015/0018715 A1 | 1/2015 | Walterspiel | |
| 2015/0094615 A1 | 4/2015 | Patton | |
| 2015/0099996 A1 | 4/2015 | Bullington et al. | |
| 2015/0257691 A1 | 9/2015 | Bullington et al. | |
| 2015/0342510 A1 | 12/2015 | Bullington et al. | |

(56) References Cited

U.S. PATENT DOCUMENTS

| | | | |
|---|---|---|---|
| 2015/0351678 | A1 | 12/2015 | Bullington et al. |
| 2015/0351679 | A1 | 12/2015 | Bullington et al. |
| 2015/0367069 | A1 | 12/2015 | Bullington et al. |
| 2016/0174888 | A1 | 6/2016 | Berthier et al. |

FOREIGN PATENT DOCUMENTS

| | | | | |
|---|---|---|---|---|
| CN | 101437450 A | 5/2009 | | |
| CN | 101352357 A | 3/2010 | | |
| CN | 101676001 A | 3/2010 | | |
| CN | 101801445 A | 8/2010 | | |
| CN | 103027727 A | 4/2013 | | |
| DE | 2 203 858 B2 | 5/1973 | | |
| DE | 2 541 494 A1 | 3/1977 | | |
| DE | 299 13 417 U1 | 12/2000 | | |
| DE | 100 38 026 A1 | 2/2001 | | |
| DE | 102 43 129 A1 | 4/2004 | | |
| EP | 0 207 304 | 1/1987 | | |
| EP | 0 448 795 | 10/1991 | | |
| EP | 0761173 | 3/1997 | | |
| EP | 0608985 | 4/1997 | | |
| EP | 0727187 | 8/2003 | | |
| EP | 1980204 | 10/2008 | | |
| WO | WO 1986/005568 | 9/1986 | | |
| WO | WO 1991/018632 | 12/1991 | | |
| WO | WO 1992/016144 | 10/1992 | | |
| WO | WO 1995/016395 | 6/1995 | | |
| WO | WO 1997/018845 | 5/1997 | | |
| WO | WO 1999/048425 | 9/1999 | | |
| WO | WO 1999/055232 | 11/1999 | | |
| WO | WO 2000/024313 | 5/2000 | | |
| WO | WO 2000/041624 | 7/2000 | | |
| WO | WO 2001/008546 | 2/2001 | | |
| WO | WO 2003/008012 | 1/2003 | | |
| WO | WO 2005/068011 | 7/2005 | | |
| WO | WO 2006/031500 | 3/2006 | | |
| WO | WO 2007/033319 | 3/2007 | | |
| WO | WO 2008/077047 | 6/2008 | | |
| WO | WO 2008/101025 | 8/2008 | | |
| WO | WO 2011/030282 A1 | 3/2011 | | |
| WO | WO 2011/069145 A2 | 6/2011 | | |
| WO | WO-2012012127 A2 * | 1/2012 | .......... | A61M 5/3129 |
| WO | WO 2013/181352 | 12/2013 | | |
| WO | WO 2014/022275 | 2/2014 | | |
| WO | WO 2014/058945 | 4/2014 | | |
| WO | WO 2014/089186 | 6/2014 | | |
| WO | WO 2014/099266 | 6/2014 | | |

OTHER PUBLICATIONS

Office Action for U.S. Appl. No. 15/088,842, dated Nov. 23, 2016, 19 pages.
Office Action for U.S. Appl. No. 15/432,310, dated Apr. 12, 2017, 12 pages.
Office Action for U.S. Appl. No. 15/435,684, dated Jun. 12, 2017, 18 pages.
Office Action for U.S. Appl. No. 15/448,891, dated Jun. 16, 2017, 23 pages.
Office Action for U.S. Appl. No. 15/457,082, dated Jun. 15, 2017, 21 pages.
Office Action for U.S. Appl. No. 15/829,018, dated Feb. 16, 2018, 24 pages.
Office Action for U.S. Appl. No. 15/829,023, dated Feb. 7, 2018, 36 pages.
Office Action for U.S. Appl. No. 15/832,055, dated Feb. 8, 2018, 21 pages.
Office Action for U.S. Appl. No. 15/832,087, dated Feb. 7, 2018, 35 pages.
Office Action for U.S. Appl. No. 14/096,826, dated Jul. 26, 2017, 11 pages.
Office Action for U.S. Appl. No. 14/728,318, dated May 19, 2017, 25 pages.
Office Action for U.S. Appl. No. 14/838,794, dated Aug. 3, 2017, 7 pages.
Extended European Search Report for European Application No. 17204012.3, dated Feb. 14, 2018.
Extended European Search Report for European Application No. 17206745.6, dated Feb. 19, 2018.
Notice of Reasons for Rejection for Japanese Application No. 2015-545813, dated Jul. 4, 2017, 8 pages.
Notification of the First Office Action for Chinese Application No. 201380040468.7, dated Jun. 30, 2016, 9 pages.
Notification of the First Office Action for Chinese Application No. 201380072185.0, dated Sep. 28, 2016, 9 pages.
Supplementary European Search Report for European Application No. 13860741.1, dated Jun. 7, 2016, 6 pages.
Supplementary European Search Report for European Application No. 13845555.5, dated Jul. 12, 2016, 9 pages.
Office Action for U.S. Appl. No. 11/955,635, dated Jul. 22, 2010, 11 pages.
Office Action for U.S. Appl. No. 11/955,635, dated Dec. 3, 2010, 11 pages.
International Search Report and Written Opinion for International Application No. PCT/US2007/087951 dated May 16, 2008, 8 pages.
Office Action for U.S. Appl. No. 13/335,241, dated Apr. 20, 2012, 12 pages.
Office Action for U.S. Appl. No. 13/458,508, dated Jul. 24, 2012, 13 pages.
Office Action for U.S. Appl. No. 13/675,295, dated May 23, 2013, 15 pages.
Office Action for U.S. Appl. No. 14/089,267, dated Jun. 19, 2014, 13 pages.
International Search Report and Written Opinion for International Application No. PCT/US2013/071491, dated Aug. 5, 2014, 9 pages.
Office Action for U.S. Appl. No. 13/954,528, dated Mar. 17, 2014, 10 pages.
Supplementary European Search Report for European Application No. 13797732.8, dated Dec. 7, 2015, 6 pages.
International Search Report and Written Opinion for International Application No. PCT/US2013/043289, dated Oct. 24, 2013, 15 pages.
Office Action for U.S. Appl. No. 14/493,796, dated Jan. 27, 2015, 7 pages.
Office Action for U.S. Appl. No. 14/494,208, dated Jan. 27, 2015, 7 pages.
International Search Report and Written Opinion for International Application No. PCT/US2013/073080, dated Feb. 18, 2014, 14 pages.
Office Action for U.S. Appl. No. 14/049,326, dated Apr. 24, 2015, 10 pages.
International Search Report and Written Opinion for International Application No. PCT/US2013/063975, dated Mar. 20, 2014, 16 pages.
Office Action for U.S. Appl. No. 13/952,964, dated Mar. 20, 2015, 11 pages.
International Search Report and Written Opinion for International Application No. PCT/US2013/052493, dated Nov. 27, 2013, 7 pages.
Arkin, C. F. et al., "Procedures for the Collection of Diagnostic Blood Specimens by Venipuncture; Approved Standard," Fifth Edition, Clinical and Laboratory Standards Institute, vol. 23, No. 32 (2003), 52 pages.
Calam, R. R., "Recommended 'Order of Draw' for Collecting Blood Specimens Into Additive-Containing Tubes," Letter to the Editor, Clinical Chemistry, 28(6):1399 (1982).
Hall, K. K. et al., "Updated Review of Blood Culture Contamination," Clinical Microbiology Reviews, 19(4):788-802 (2006).
Kim, J. Y. et al., "The Sum of the Parts is Greater Than the Whole: Reducing Blood Culture Contamination," Annals of Internal Medicine, 154:202-203 (2011).
Levin, P. D. et al., "Use of the Nonwire Central Line Hub to Reduce Blood Culture Contamination," Chest, 143(3):640-645 (2013).
Medical Surgical Systems Catalogue (Canadian Version), BD Medical, 2010, 51 pages.

(56) References Cited

OTHER PUBLICATIONS

Order of Draw for Multiple Tube Collections, LabNotes, a newsletter from BD Diagnostics,—Preanalytical Systems, 17(1):3 (2007).
Patton, R. G. et al., "Innovation for Reducing Blood Culture Contamination: Initial Specimen Diversion Technique," Journal of Clinical Microbiology, 48(12):4501-4503 (2010).
Proehl, J. A. et al., "Clinical Practice Guideline: Prevention of Blood Culture Contamination, Full Version," 2012 ENA Emergency Nurses Resources Development Committee, Emergency Nurses Association (Dec. 2012), 14 pages.
Schuur, J., "Blood Cultures: When Do they Help and When Do They Harm?" Brigham & Women's Hospital, Department of Emergency Medicine, (Jun. 21-23, 2012), 42 pages.
Sibley, C. D. et al., "Molecular Methods for Pathogen and Microbial Community Detection and Characterization: Current and Potential Application in Diagnostic Microbiology," Infection, Genetics and Evolution 12:505-521 (2012).
Stohl, S. et al., "Blood Cultures at Central Line Insertion in the Intensive Care Unit: Comparison with Peripheral Venipuncture," Journal of Clinical Microbiology, 49(7):2398-2403 (2011).
Wagner et al., "Diversion of Initial Blood Flow to Prevent Whole-Blood Contamination by Skin Surface Bacteria: an in vitro model," Transfusion, 40:335-338 (2000).
Office Action for U.S. Appl. No. 14/498,102, dated Sep. 24, 2018, 18 pages.
Office Action for U.S. Appl. No. 15/829,015, dated Feb. 6, 2018, 24 pages.
Office Action for U.S. Appl. No. 14/712,431, dated Sep. 14, 2018, 10 pages.
Office Action for U.S. Appl. No. 15/832,091, dated Feb. 22, 2018, 16 pages.
Office Action for U.S. Appl. No. 14/662,676, dated Sep. 5, 2018, 25 pages.
Office Action for U.S. Appl. No. 15/854,273, dated Sep. 7, 2018, 15 pages.
Office Action for U.S. Appl. No. 14/096,826, dated Mar. 8, 2018, 16 pages.
Office Action for U.S. Appl. No. 14/728,318, dated Jan. 8, 2018, 36 pages.
Examination Report for United Kingdom Application No. GB1805101.1, dated May 25, 2018, 8 pages.
International Search Report and Written Opinion for International Application No. PCT/US2018/36910, dated Sep. 4, 2018, 21 pages.
Office Action for U.S. Appl. No. 14/712,437 dated Oct. 25, 2018, 20 pages.
Office Action for U.S. Appl. No. 15/854,273, dated Mar. 15, 2019, 19 pages.
Office Action for U.S. Appl. No. 14/728,318, dated Dec. 20, 2018, 26 pages.
Office Action for U.S. Appl. No. 16/255,055, dated Mar. 18, 2019, 16 pages.
Office Action for U.S. Appl. No. 15/925,159, dated Nov. 26, 2018, 11 pages.
Office Action for U.S. Appl. No. 15/925,159, dated May 14, 2019, 15 pages.
International Search Report and Written Opinion for International Application No. PCT/US2016/050380, dated Dec. 1, 2016, 6 pages.
International Search Report and Written Opinion for International Application No. PCT/US2018/050621, dated Feb. 26, 2018, 11 pages.
International Search Report and Written Opinion for International Application No. PCT/US2018/064561, dated Feb. 11, 2019, 9 pages.
Notice of Reasons for Rejection for Japanese Application No. 2018-086721, w/English translation, dated Mar. 15, 2019, 6 pages.
Office Action for Canadian Application No. 2,875,118, dated Mar. 21, 2019, 5 pages.
Office Action for U.S. Appl. No. 16/299,962, dated May 2, 2019, 14 pages.
Office Action for U.S. Appl. No. 15/854,273, dated Jan. 13, 2020, 13 pages.
Extended European Search Report for EP Application No. 19156636.3, dated Aug. 27, 2019, 7 pages.
International Search Report and Written Opinion for International Application No. PCT/US2019/034626, dated Aug. 22, 2019, 16 pages.
Barnard, D. R. & Arthur, M. M., "Fibronectin (cold insoluble globulin) in the neonate," Clinical and Laboratory Observations, 102(3): 453-455 (1983).
Baxter, "IV Tubing and Access Devices" authored by and published by Baxter, dated Nov. 6, 2006, 105 pages.
BD Saf-T-Intima Closed IV Catheter System, Becton, Dickinson and Company, 2015 Brochure. Retrieved from the Internet (Sep. 11, 2019) <https://www.bd.com/en-us/offerings/capabilities/infusion-therapy/iv-catheters/bd-saf-tintima-closed-iv-catheter-system>, 2 pages.
BD Vacutainer Passive Shielding Blood Collection Needle Brochure; Becton Dickinson and Company (2005), 2 pages.
Brecher, M. E. et al., "Bacterial Contamination of Blood Components," Clinical Microbiology Reviews, 18(1):195-204 (2005).
Cartridge and Test Information, Abbott, Art: 714258-010 Rev. Date: Aug 15, 2016, 6 pages.
Challiner, A. et al., Queen Alexandra Hospital, Portsmouth P06 3LY, "Venous/arterial blood management protection system," Correspondence, p. 169.
De Korte, D. et al., "Diversion of first blood volume results in a reduction of bacterial contamination for whole-blood collections," Vox Sanguinis, 83:13-16 (2002).
De Korte, D. et al., "Effects of skin disinfection method, deviation bag, and bacterial screening on clinical safety of platelet transfusions in the Netherlands," Transfusion, 46: 476-485 (2006).
Edwards Lifesciences, "Conservation. Safety. Simplicity. Edwards VAMP and VAMP Jr. Systems," 2002 Brochure. Retrieved from the Internet (Sep. 11, 2019) <https://www.medline.com/media/catalog/Docs/MKT/VAMPSYSTEMBROCHURE.PDF>, 4 pages.
Ernst, D. J. et al., "NCCLS simplifies the order of draw: a brief history," MLO, 26-27 (2004).
Gottlieb, T., "Hazards of Bacterial Contamination of Blood Products," Anaesth Intens Care, 21: 20-23 (1993).
Hillyer, C. D. et al., "Bacterial Contamination of Blood Components Risks, Strategies, and Regulation," Hematology, 575-589 (2003).
Pall Corp., "Leukotrap Filtration Systems for Whole Blood Derived Platelets: Leukotrap RC PL and Leukotrap PL Systems," 2005 Brochure, 2 pages.
Li, Y. et al., "Direct labeling and visualization of blood vessels with lipophilic carbocyanine dye Dil," Nature Protocols, 3(11): 1703-1708 (2008).
Liumbruno, G. M. et al., "Reduction of the risk of bacterial contamination of blood components through diversion of the first part of the donation of blood and blood components," Blood Transfus, 7: 86-93 (2009).
Mayer, G. A., "A Method for the Reliable Determination of Clotting Time in Whole Blood," Can Med Assoc J., 72(12): 927-929 (1955).
McDonald, C. P., "Interventions Implemented to Reduce the Risk of Transmission of Bacteria by Transfusion in the English National Blood Service," Transfus Med Hemother, 38:255-258 (2011).
Meissner, G. F. et al., "A Method Based on the Use of Whole Venous Blood in Capillary Tubes," American Journal of Clinical Pathology, 33(2): 29-31 (1963).
Murphy, M., "Better Blood Transfusion," Journal of the Intensive Core Society, 4(3): 78-80 (2003).
Napolitano, M. et al., "Quality control of bacterial contamination of blood components: the feasibility of diversion system testing," Blood Transfus, 2: 231-232 (2004).
Norberg, A. et al., "Contamination Rates of Blood Cultures Obtained by Dedicated Phlebotomy vs Intravenous Catheter," JAMA, 289(6): 726-729 (2003).
Page, C. et al., "Blood conservation devices in critical care: a narrative review," Annals of Intensive Care, 3:14 (2013), 6 pages.
Palavecino, E. L. et al., "Detecting Bacterial Contamination in Platelet Products," Clin. Lab., 52:443-456 (2006).

(56) References Cited

OTHER PUBLICATIONS

Perez, P. et al., "Multivariate analysis of determinants of bacterial contamination of whole-blood donations," Vox Sanguinis, 82:55-60 (2002).

Quilici, N. et al., "Differential Quantitative Blood Cultures in the Diagnosis of Catheter-Related Sepsis in Intensive Care Units," Clinical Infectious Diseases 25:1066-1070 (1997).

Sheppard, C. A. et al., "Bacterial Contamination of Platelets for Transfusion: Recent Advances and Issues," LabMedicine, 36(12):767-770 (2005).

Shulman, G., "Quality of Processed Blood for Autotransfusion," The Journal of Extra-Corporeal Technology, 32(1): 11-19 (2000).

Tang, M. et al., "Closed Blood Conservation Device for Reducing Catheter-Related Infections in Children After Cardiac Surgery," Critical Care Nurse, 34(5): 53-61 (2014).

Wang, P. et al., "Strategies on Reducing Blood Culture Contamination," Reviews in Medical Microbiology, 23:63-66 (2012).

Weinbaum, F. I. et al., "Doing It Right the First Time: Quality Improvement and the Contaminant Blood Culture," Journal of Clinical Microbiology, 35(3): 563-565 (1997).

Weinstein, M. P., "Current Blood Culture Methods and Systems: Clinical Concepts, Technology, and Interpretation of Results," Clinical Infectious Diseases, 23: 40-46 (1996).

Weinstein, M. P., "Minireview: Blood Culture Contamination: Persisting Problems and Partial Progress," Journal of Clinical Microbiology, 41(6): 2275-2278 (2003).

Weinstein, M. P. et al., "The Clinical Significance of Positive Blood Cultures in the 1990s: A Prospective Comprehensive Evaluation of the Microbiology, Epidemiology, and Outcome of Bacteremia and Fungemia in Adults," Clinical Infectious Diseases, 24:584-602 (1997).

Ziegler, et al., "Controlled Clinical Laboratory Comparison of Two Supplemented Aerobic and Anaerobic Media Used in Automated Blood Culture Systems to Detect Bloodstream Infections," J. Clinical Microbiology, 36(3):657-661 (1998).

Zimmon, D. S. et al., "Effect of Portal Venous Blood Flow Diversion on Portal Pressure," J Clin Invest, 65(6): 1388-1397 (1980).

Zundert, A. V., "New Closed IV Catheter System," Acta Anaesth. Belg., 56: 283-285 (2005).

\* cited by examiner

FLUID DIVERSION MECHANISM FOR BODILY-FLUID SAMPLING

CROSS-REFERENCE TO RELATED APPLICATIONS

This application is a continuation of U.S. patent application Ser. No. 13/952,964, entitled, "Fluid Diversion Mechanism for Bodily-Fluid Sampling," filed on Jul. 29, 2013, which claims priority to and the benefit of U.S. Provisional Patent Application Ser. No. 61/678,404, entitled, "Fluid Diversion Mechanism for Bodily-Fluid Sampling," filed on Aug. 1, 2012, the disclosures of which are incorporated herein by reference in their entireties.

BACKGROUND

Embodiments described herein relate generally to the parenteral procurement of bodily-fluid samples, and more particularly to devices and methods for parenterally-procuring bodily-fluid samples with reduced contamination from microbes and/or other contaminants exterior to the bodily-fluid source, such as dermally-residing microbes.

Health care practitioners routinely perform various types of microbial tests on patients using parenterally-obtained bodily-fluids. In some instances, patient samples (e.g., bodily-fluids) are tested for the presence of one or more potentially undesirable microbes, such as bacteria, fungi, or yeast (e.g., *Candida*). Microbial testing may include incubating patient samples in one or more sterile vessels containing culture media that is conducive to microbial growth. Generally, when microbes tested for are present in the patient sample, the microbes flourish over time in the culture medium. After a pre-determined amount of time (e.g., a few hours to several days), the culture medium can be tested for the presence of the microbes. The presence of microbes in the culture medium suggests the presence of the same microbes in the patient sample which, in turn, suggests the presence of the same microbes in the bodily-fluid of the patient from which the sample was obtained. Accordingly, when microbes are determined to be present in the culture medium, the patient may be prescribed one or more antibiotics or other treatments specifically designed to treat or otherwise remove the undesired microbes from the patient.

In some instances, however, patient samples can become contaminated during procurement. For example, contamination of a patient sample may occur by the transfer of microbes from a bodily surface (e.g., dermally-residing microbes) dislodged during needle insertion into a patient and subsequently transferred to a culture medium with the patient sample. The bodily surface microbes may be dislodged either directly or via dislodged tissue fragments, hair follicles, sweat glands and other adnexal structures. The transferred microbes may thrive in the culture medium and eventually yield a positive microbial test result, thereby falsely indicating the presence of such microbes in vivo. Such inaccurate results are a concern when attempting to diagnose or treat a suspected illness or condition. For example, false positive results from microbial tests may result in the patient being unnecessarily subjected to one or more anti-microbial therapies, which may cause serious side effects to the patient including, for example, death, as well as produce an unnecessary burden and expense to the health care system.

As such, a need exists for improved bodily-fluid transfer devices and methods that reduce microbial contamination in bodily-fluid test samples.

SUMMARY

Devices for parenterally-procuring bodily-fluid samples with reduced contamination from microbes exterior to the bodily-fluid source, such as dermally-residing microbes, are described herein. In some embodiments, a device includes a pre-sample reservoir, an actuator mechanism, and a diverter. The pre-sample reservoir is configured to be fluidically coupled to a needle to receive and isolate a predetermined volume of bodily-fluid withdrawn from the patient. The actuator mechanism is operably coupled to the pre-sample reservoir such that, when actuated, a negative pressure is formed in the pre-sample reservoir that urges the bodily-fluid to flow into the pre-sample reservoir. The diverter is configured to selectively control fluid flow between the needle and the pre-sample reservoir. The diverter includes a flow control mechanism that defines a first fluid flow path and a second fluid flow path. The diverter is configured to be moved between a first configuration in which the bodily-fluid can flow through the first fluid flow path to the pre-sample reservoir, and a second configuration in which the bodily-fluid can flow through the second fluid flow path to a sample reservoir coupled to the diverter.

DETAILED DESCRIPTION

Figure 1:
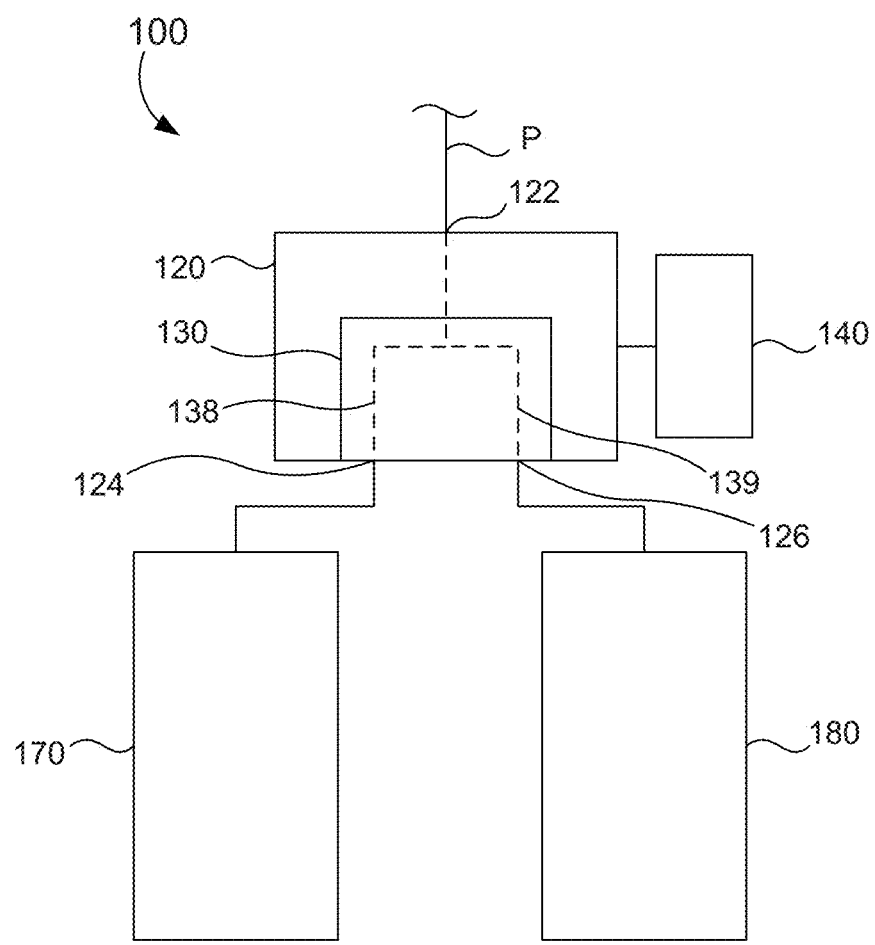
FIG. 1 is a schematic illustration of a bodily-fluid transfer device according to an embodiment.
Figure 2:
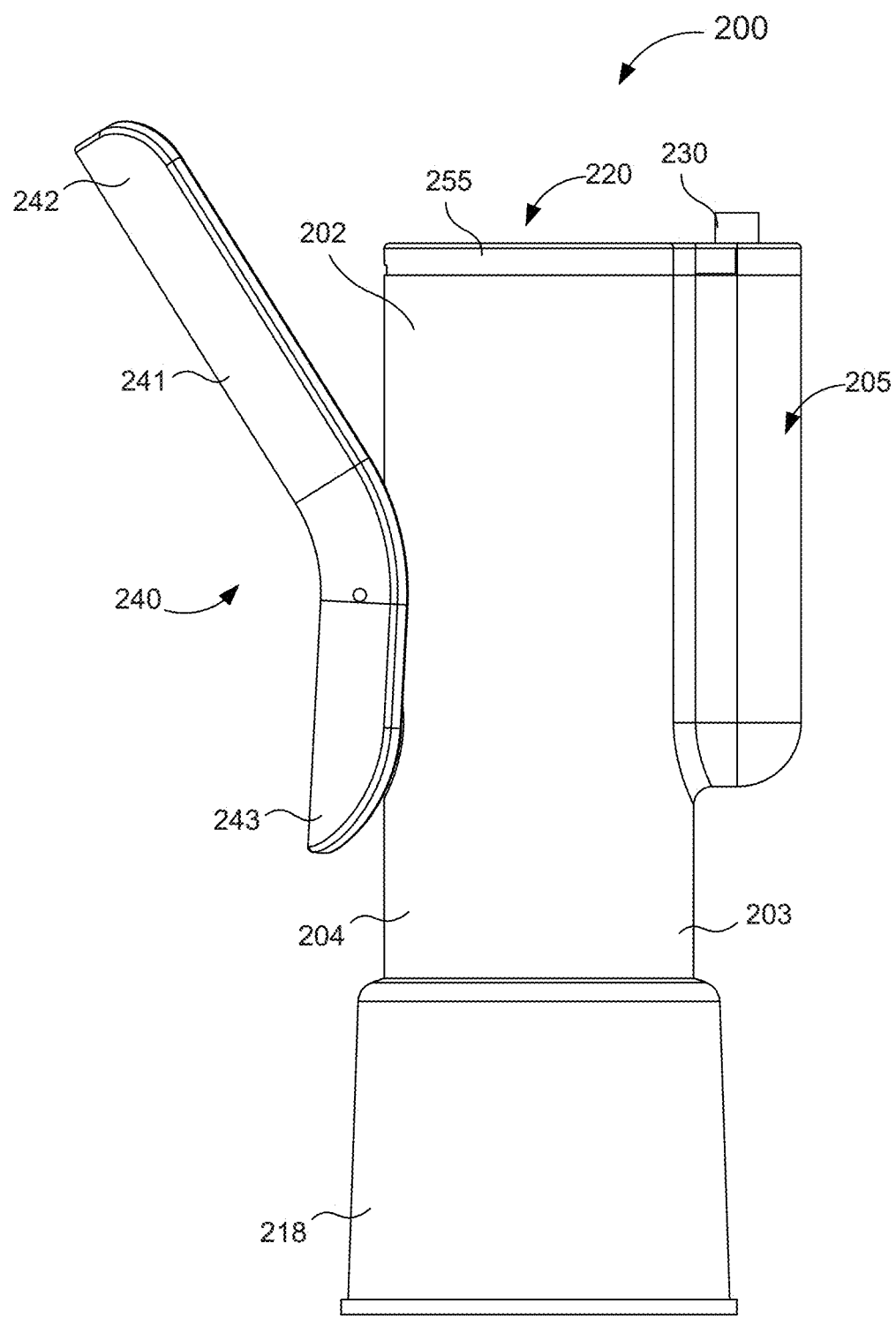
FIG. 2 is a front view of a bodily-fluid transfer device according to an embodiment, in a first configuration.
Figure 3:
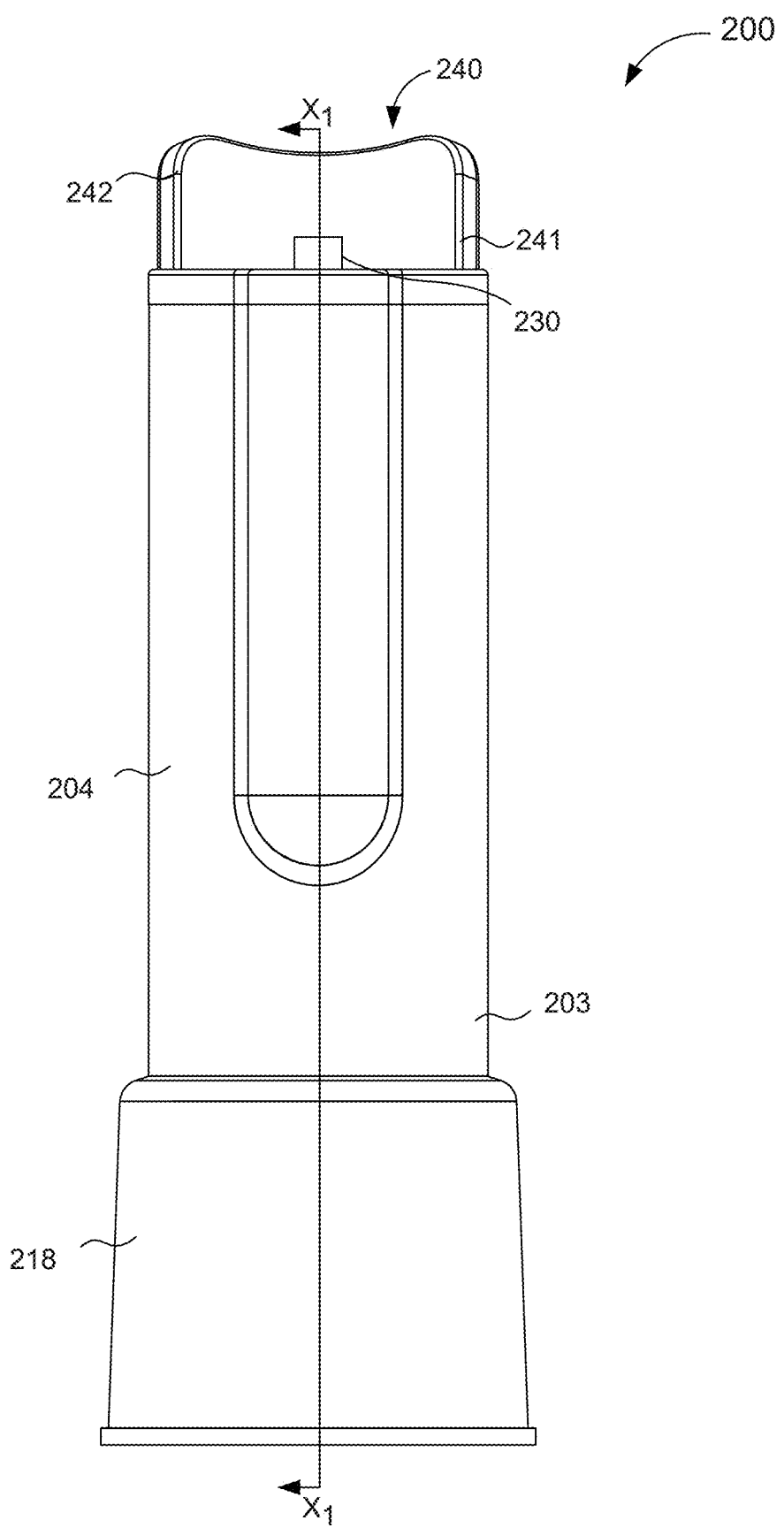
FIG. 3 is a side view of the bodily-fluid transfer device of FIG. 2.
Figure 4:
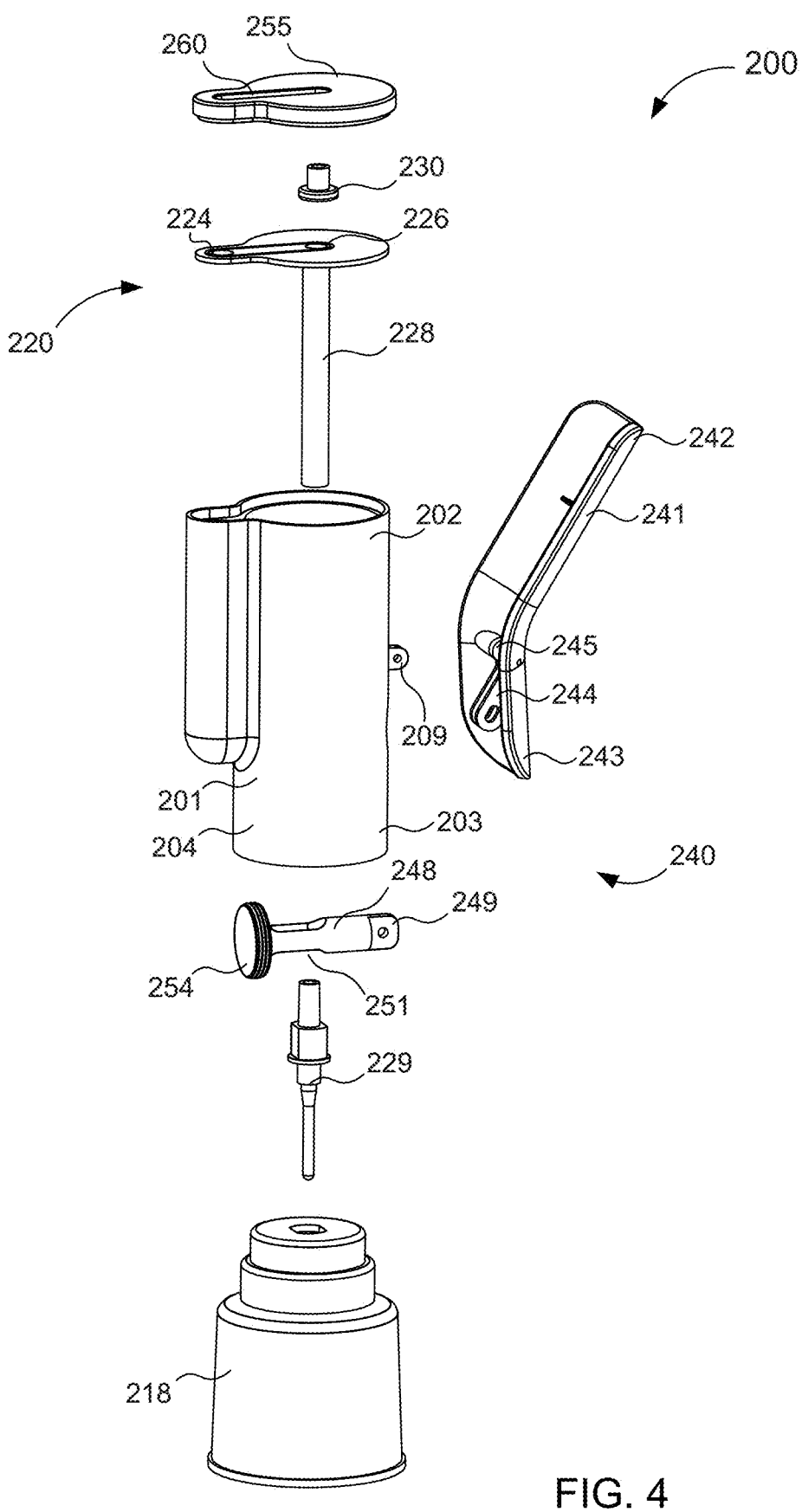
FIG. 4 is an exploded view of the bodily-fluid transfer device of FIG. 2.

Devices for parenterally-procuring bodily-fluid samples with reduced contamination from microbes exterior to the bodily-fluid source, such as dermally-residing microbes, are described herein. In some embodiments, a device includes a pre-sample reservoir, an actuator mechanism, and a diverter. The pre-sample reservoir is configured to be fluidically coupled to a needle to receive and isolate a predetermined volume of bodily-fluid withdrawn from the patient. The actuator mechanism is operably coupled to the pre-sample reservoir such that, when actuated, a negative pressure is formed in the pre-sample reservoir that urges the bodily-fluid to flow into the pre-sample reservoir. The diverter is configured to selectively control fluid flow between the needle and the pre-sample reservoir. The diverter includes a flow control mechanism that defines a first fluid flow path and a second fluid flow path. The diverter is configured to be moved between a first configuration in which the bodily-fluid can flow through the first fluid flow path to the pre-sample reservoir, and a second configuration in which the bodily-fluid can flow through the second fluid flow path to a sample reservoir coupled to the diverter.

In some embodiments, a method for procuring bodily-fluid samples from a patient using a parenterally sampling device that includes an actuation mechanism, a flow control mechanism and a pre-sample reservoir includes establishing fluid communication between a patient and the pre-sample reservoir. A first volume of bodily-fluid is withdrawn by moving the actuation mechanism from a first position to a second position to create a negative pressure in the pre-sample reservoir. The flow control mechanism is moved from a first configuration in which bodily-fluid is allowed to flow through a first flow path from the patient to the pre-sample reservoir to a second configuration in which bodily-fluid is allowed to flow through a second flow path from the patient to a sample reservoir.

In some embodiments, a bodily-fluid sampling device includes a pre-sample reservoir, a diverter mechanism, and an actuator. The pre-sample reservoir is configured to be fluidically coupled to a needle. The pre-sample is configured to have a negative pressure and configured to receive and isolate a predetermined volume of bodily-fluid withdrawn from a patient, via the needle. The diverter mechanism is configured to be fluidically coupled to the pre-sample reservoir. The diverter mechanism includes a flow control mechanism configured for rotational movement between a first configuration in which the flow control mechanism and the diverter mechanism collectively define a first fluid flow path between the needle and the pre-sample reservoir and a second configuration in which the flow control mechanism and the diverter mechanism collectively define a second fluid flow path between the needle and a sample reservoir operably coupled to the diverter mechanism. The actuator is rotatably coupled to the diverter mechanism and configured to be rotated from a first position, wherein the flow control mechanism is in the first configuration, to a second position, wherein the flow control mechanism is in the second configuration.

In some embodiments, a method for procuring bodily-fluid samples from a patient using a parenterally sampling device that has a flow control mechanism and an integrated pre-sample reservoir having a negative pressure includes inserting a needle into the patient while the flow control mechanism is in a first configuration. The first configuration of the flow control mechanism is operable in preventing bodily-fluid from flowing from the patient to the integrated pre-sample reservoir. The flow control mechanism is moved from the first configuration to a second configuration. The second configuration of the flow control mechanism is operable in allowing bodily-fluid to flow through a first flow path defined at least in part by the flow control mechanism to the pre-sample reservoir. After a predetermined volume of bodily-fluid has been received in the pre-sample reservoir, the method includes moving the flow control mechanism from the second configuration to a third configuration. The third configuration of the flow control mechanism is operable in allowing bodily-fluid to flow through a second flow path defined at least in part by the flow control mechanism to a sample reservoir.

In some embodiments, an apparatus includes a diverter, a flow control mechanism, and an actuator mechanism. The diverter defines an inlet port, a first outlet port, and a second outlet port. The first outlet port is fluidically coupled to a first fluid reservoir and the second outlet port is fluidically coupled to a second reservoir, fluidically isolated from the first fluid reservoir. The flow control mechanism is configured to be operably coupled to the diverter. In use, the flow control mechanism is moved between a first configuration, in which a flow of bodily-fluid can enter the first fluid reservoir, and a second configuration, in which a flow of bodily-fluid can enter the second fluid reservoir.

In some embodiments, a bodily-fluid transfer device can be configured to selectively divert a first, predetermined amount of a flow of a bodily-fluid to a first reservoir before permitting the flow of a second amount of the bodily-fluid into a second reservoir. In this manner, the second amount of bodily-fluid can be used for diagnostic or other testing, while the first amount of bodily-fluid, which may contain microbes from a bodily surface, is isolated from the second amount of the bodily-fluid. The first amount of bodily fluid can be discarded or used for non-culture tests, such as one or more biochemical tests, blood counts, immunodiagnostic tests, cancer-cell detection tests, and the like where microbes from a bodily surface do not affect the test results.

As used in this specification and the appended claims, "bodily-fluid" can include any fluid obtained from a body of a patient, including, but not limited to, blood, cerebrospinal fluid, urine, bile, lymph, saliva, synovial fluid, serous fluid, pleural fluid, amniotic fluid, and the like, or any combination thereof.

As used herein, the term "set" can refer to multiple features or a singular feature with multiple parts. For example, when referring to set of walls, the set of walls can be considered as one wall with distinct portions, or the set of walls can be considered as multiple walls. Similarly stated, a monolithically constructed item can include a set of walls. Such a set of walls can include, for example, multiple portions that are discontinuous from each other. A set of walls can also be fabricated from multiple items that are produced separately and later joined together (e.g., via a weld, an adhesive or any suitable method).

As used herein, the words "proximal" and "distal" refer to the direction closer to and away from, respectively, a user who would place the device into contact with a patient. Thus, for example, the end of a device first touching the body of the patient would be the distal end, while the opposite end of the device (e.g., the end of the device being manipulated by the user) would be the proximal end of the device.

FIG. 1 is a schematic illustration of a portion of a bodily-fluid transfer device 100, according to an embodiment. Generally, the bodily-fluid transfer device 100 (also referred to herein as "fluid transfer device" or "transfer device") is configured to permit the withdrawal of bodily-fluid from a patient such that a first portion, amount, or volume of the withdrawn fluid is diverted away from a second portion, amount, or volume of the withdrawn fluid that is to be used as a biological sample, such as for testing for the purpose of medical diagnosis and/or treatment where contamination from microbes or other contaminants exterior to the bodily-fluid source dermally-residing microbes) can affect test results. In other words, the transfer device 100 is configured to transfer a first, predetermined amount of a bodily-fluid to a first collection reservoir and a second amount of bodily-fluid to one or more bodily-fluid collection reservoirs that are fluidically isolated from the first collection reservoir, as described in more detail herein.

The transfer device 100 includes a diverter 120, a first reservoir 170, and a second reservoir 180, fluidically isolated from the first reservoir 170. The diverter 120 includes an inlet port 122 and two or more outlet ports, such as a first outlet port 124 and a second outlet port 126, as shown in FIG. 1. The inlet port 122 is configured to be fluidically coupled to a medical device defining a pathway P for withdrawing and/or conveying the bodily-fluid from the patient to the transfer device 100. For example, the inlet port 122 can be fluidically coupled to a needle, a fluid deliver member, or other lumen-containing device (e.g., flexible sterile tubing). In this manner, the diverter 120 can receive the bodily-fluid from the patient via the needle, other lumen-containing devices (e.g., cannula, catheters, etc.), or any other device suitable for collection of bodily-fluid samples from a patient.

The first outlet port 124 of the diverter 120 is configured to be fluidically coupled to the first reservoir 170. In some embodiments, the first reservoir 170 is monolithically formed with the first outlet port 124 and/or a portion of the diverter 120. In other embodiments, the first reservoir 170 can be mechanically and fluidically coupled to the diverter 120 via an adhesive, a resistance fit, a mechanical fastener, any number of mating recesses, a threaded coupling, and/or any other suitable coupling or combination thereof. Similarly stated, the first reservoir 170 can be physically (e.g., mechanically) coupled to the diverter 120 such that an interior volume defined by the first reservoir 170 is in fluid communication with the first outlet port 124 of the diverter 120. In still other embodiments, the first reservoir 170 can be operably coupled to the first outlet port 124 of the diverter 120 via an intervening structure (not shown in FIG. 1), such as a flexible sterile tubing. More particularly, the intervening structure can define a lumen configured to place the first reservoir 170 in fluid communication with the first outlet port 124.

The first reservoir 170 is configured to receive and contain the first, predetermined amount of the bodily-fluid. In some embodiments, the first reservoir 170 is configured to contain the first amount of the bodily-fluid such that the first amount is fluidically isolated (or sequestered) from a second amount of the bodily-fluid that is subsequently withdrawn from the patient. The first reservoir 170 can be any suitable reservoir for containing a bodily-fluid, such as a pre-sample reservoir described in detail in U.S. Patent Publication No. 2008/0145933 ("the '933 Publication"), the disclosure of which is incorporated herein by reference in its entirety. For example, the first reservoir can be an evacuated sample tube (e.g., BD Vacutainer®) of sufficient size to collect the first amount of bodily fluid. As used in this specification, the terms "first, predetermined amount" and "first amount" describe an amount of bodily-fluid configured to be received or contained by the first reservoir 170. Furthermore, while the term "first amount" does not explicitly describe a predetermined amount, it should be understood that the first amount is the first, predetermined amount unless explicitly described differently.

The second outlet port 126 of the diverter 120 is configured to be fluidically coupled to the second reservoir 180. In some embodiments, the second reservoir 180 is monolithically formed with the second outlet port 126 and/or a portion of the diverter 120. In other embodiments, the second reservoir 180 can be mechanically coupled to the second outlet port 126 of the diverter 120 or operably coupled to the second outlet port 126 via an intervening structure (not shown in FIG. 1), such as described above with reference to the first reservoir 170. The second reservoir 180 is configured to receive and contain the second amount of the bodily-fluid. For example, the second amount of bodily-fluid can be an amount withdrawn from the patient subsequent to withdrawal of the first amount. In some embodiments, the second reservoir 180 is configured to contain the second amount of the bodily-fluid such that the second amount is fluidically isolated from the first amount of the bodily-fluid.

The second reservoir 180 can be any suitable reservoir for containing a bodily-fluid, including, for example, a sample reservoir as described in the '933 Publication incorporated by reference above. As used in this specification, the term "second amount" describes an amount of bodily-fluid configured to be received or contained by the second reservoir 180. In some embodiments, the second amount can be any suitable amount of bodily-fluid and need not be predetermined. In other embodiments, the second amount received and contained by the second reservoir 180 is a second, predetermined amount.

In some embodiments, the first reservoir 170 and the second reservoir 180 can be coupled to (or formed with) the diverter 120 in a similar manner. In other embodiments, the first reservoir 170 and the second reservoir 180 need not be similarly coupled to the diverter 120. For example, in some embodiments, the first reservoir 170 can be monolithically formed with the diverter 120 (e.g., the first outlet port 124) and the second reservoir 180 can be operably coupled to the diverter 120 (e.g., the second outlet port 126) via an intervening structure, such as a flexible sterile tubing. In other embodiments, the first reservoir 170 can be monolithically formed with the diverter 120 and the second fluid reservoir 180 can be removably coupled to the diverter 120.

As shown in FIG. 1, the transfer device 100 further includes an actuator 140 and a flow control mechanism 130 first lumen 138 second lumen 139. In some embodiments, the actuator 140 can be included in or otherwise operably coupled to the diverter 120. In this manner, the actuator 140 can be configured to control a movement of the flow control mechanism 130 (e.g., between a first configuration and a second configuration). For example, the actuator 140 can be movable between a first position corresponding to the first configuration of the flow control mechanism 130, and a second position, different than the first position, corresponding to the second configuration of the flow control mechanism 130. In some embodiments, the actuator 140 is configured for uni-directional movement. For example, the actuator 140 can be moved from its first position to its second position, but cannot be moved from its second position to its first position. In this manner, the flow control mechanism 130 is prevented from being moved to its second configuration before its first configuration, thus requiring that the first amount of the bodily-fluid be directed to the first reservoir 170 and not the second reservoir 180, as described in further detail herein.

The flow control mechanism 130 defines a first lumen 138 and a second lumen 139. The flow control mechanism 130 is configured such that when in the first configuration, the first lumen 138 fluidically couples the inlet port 122 to the first outlet port 124 and when in the second configuration, the second lumen 139 fluidically couples the inlet port 122 to the second outlet port 126. Said another way, when in the first configuration, the first lumen 138 defines at least a portion of a first fluid flow path between the inlet port 122 and the first outlet port 124, and when in the second configuration, the second lumen 139 defines at least a portion of a second fluid flow path between the inlet port 122 and the second outlet port 126. In some embodiments, the actuator 140 is coupled to the flow control mechanism 130 and is configured to move the flow control mechanism 130 in a translational motion between the first configuration and the second configuration. For example, in some embodiments, the flow control mechanism 130 can be in the first configuration when the flow control mechanism 130 is in a distal position relative to the transfer device 100. In such embodiments, the actuator 140 can be actuated to move the flow control device 130 in the proximal direction to a proximal position relative to the transfer device 100, thereby placing the flow control mechanism 130 in the second configuration. In other embodiments, the actuator 140 can be actuated to move the flow control mechanism 130 in a rotational motion between the first configuration and the second configuration.

Accordingly, when the flow control mechanism 130 is in the first configuration, the second outlet port 126 is fluidically isolated from the inlet port 122. Similarly, when the flow control mechanism 130 is in the second configuration, the first outlet port 124 is fluidically isolated from the inlet port 122. In this manner, the flow control mechanism 130 can direct, or divert the first amount of the bodily-fluid to the first reservoir 170 via the first outlet port 124 when the flow control mechanism 130 is in the first configuration and can direct, or divert the second amount of the bodily-fluid to the second reservoir 180 via the second outlet port 126 when the flow control mechanism 130 is in the second configuration.

In some embodiments, at least a portion of the actuator 140 can be operably coupled to the first reservoir 170, in this manner, the actuator 140 (or at least the portion of the actuator 140) can be configured to introduce or otherwise facilitate the development of a vacuum within the first reservoir 170, thereby initiating flow of the bodily-fluid through the transfer device 100 and into the first reservoir 170 when the diverter 120 is in its first configuration. The actuator 140 can include any suitable mechanism for actuating the transfer device 100 (e.g., at least the flow control mechanism 130) such as, for example, a rotating disc, a plunger, a slide, a dial, a button, a handle, a lever, and/or any other suitable mechanism or combination thereof. Examples of suitable actuators are described in more detail herein with reference to specific embodiments.

In some embodiments, the diverter 120 can be configured such that the first amount of bodily-fluid need be conveyed to the first reservoir 170 before the diverter 120 will permit the flow of the second amount of bodily-fluid to be conveyed through the diverter 120 to the second reservoir 180. In this manner, the diverter 120 can be characterized as requiring compliance by a health care practitioner regarding the collection of the first, predetermined amount (e.g., a pre-sample) prior to a collection of the second amount (e.g., a sample) of bodily-fluid. Similarly stated, the diverter 120 can be configured to prevent a health care practitioner from collecting the second amount, or the sample, of bodily-fluid into the second reservoir 180 without first diverting the first amount, or pre-sample, of bodily-fluid to the first reservoir 170. In this manner, the health care practitioner is prevented from including (whether intentionally or unintentionally) the first amount of bodily-fluid, which is more likely to contain bodily surface microbes (for example, dermally-residing microbes), in the bodily-fluid sample to be used for analysis. In other embodiments, the fluid transfer device 100 need not include a forced-compliance feature or component.

In some embodiments, the actuator 140 can have a third position, different than the first and second positions, which can correspond to a third configuration of the flow control mechanism 130. When in the third configuration, the flow control mechanism 130 can fluidically isolate the inlet port 122 from both the first outlet port 124 and the second outlet port 126 simultaneously. Therefore, when the flow control mechanism 130 is in its third configuration, flow of bodily-fluid from the inlet port 122 to either the first reservoir 170 or the second reservoir 180 is prevented. In use, for example, the actuator 140 can be actuated to place the flow control mechanism 130 in the first configuration such that a bodily-fluid can flow from the inlet port 122 to the first reservoir 170, then moved to the second configuration such that the bodily-fluid can flow from the inlet port 122 to the second reservoir 180, then moved to the third configuration to stop the flow of bodily-fluid into and/or through the diverter 120. In some embodiments, the flow control mechanism 130 can be moved to the third configuration between the first configuration and the second configuration. In some embodiments, the flow control mechanism 130 can be in the third configuration before being moved to either of the first configuration or the second configuration. In some embodiments, the flow control mechanism 130 can be moved between four configurations. For example, the flow control mechanism 130 can be disposed in the third configuration and moved through the first configuration and second configuration to the fourth configuration. In such embodiments, the fourth configuration can function similarly to the third configuration to fluidically isolate the inlet port 122 from the first outlet port 124 and the second outlet portion 126.

In some embodiments, one or more portions of the transfer device 100 are disposed within a housing (not shown in FIG. 1). For example, in some embodiments, at least a portion of one or more of the diverter 120, the first reservoir 170, and the actuator 140 can be disposed within the housing. In such an embodiment, at least a portion of the actuator 140 is accessible through the housing. Examples of suitable housings are described in more detail herein with reference to specific embodiments.

FIGS. 2-9 illustrate a transfer device 200 according to an embodiment. The transfer device 200 includes a housing 201, a diverter 220, and an actuator 240. The transfer device 200 can be any suitable shape, size, or configuration. For example, while shown in FIGS. 2 and 3 as being substantially cylindrical, the transfer device 200 can be square, rectangular, polygonal, and/or any other non-cylindrical shape.

The housing 201 includes a proximal end portion 202, a distal end portion 203, a first set of walls 204, and a second set of wall 212 (also referred to herein as "inner walls" 212). The distal end portion 203 of the housing 201 is coupled to a container shroud 218 configured to receive at least a portion of an external fluid reservoir (not shown in FIGS. 2-9). The container shroud 218 can be coupled to the housing 201 in any suitable manner. For example, in some embodiments, a portion of the container shroud 218 can form a friction fit within a portion of the housing 201. In some embodiments, the container shroud 218 can be coupled to the housing 201 via a threaded coupling, an adhesive, a snap fit, a mechanical fastener and/or any other suitable coupling method. In other embodiments, the container shroud 218 is monolithically formed with the housing 201. The container shroud 218 is configured to house a portion of an outlet adapter 229 (FIG. 4) such that when the external fluid reservoir is disposed within the container shroud 218, the external reservoir can be placed in fluid communication with the outlet adapter 229, as described in further detail herein.

The proximal end portion 202 of the housing 201 receives the diverter 220 and is coupled to a cap 255. The cap 255 is configured to substantially enclose a portion of the housing 201 (see for example, the exploded view of FIG. 3). Similarly stated, the cap 255 is coupled to the proximal end portion 202 of the housing 201 such that the proximal end portion 202 is substantially closed.

Figure 5:
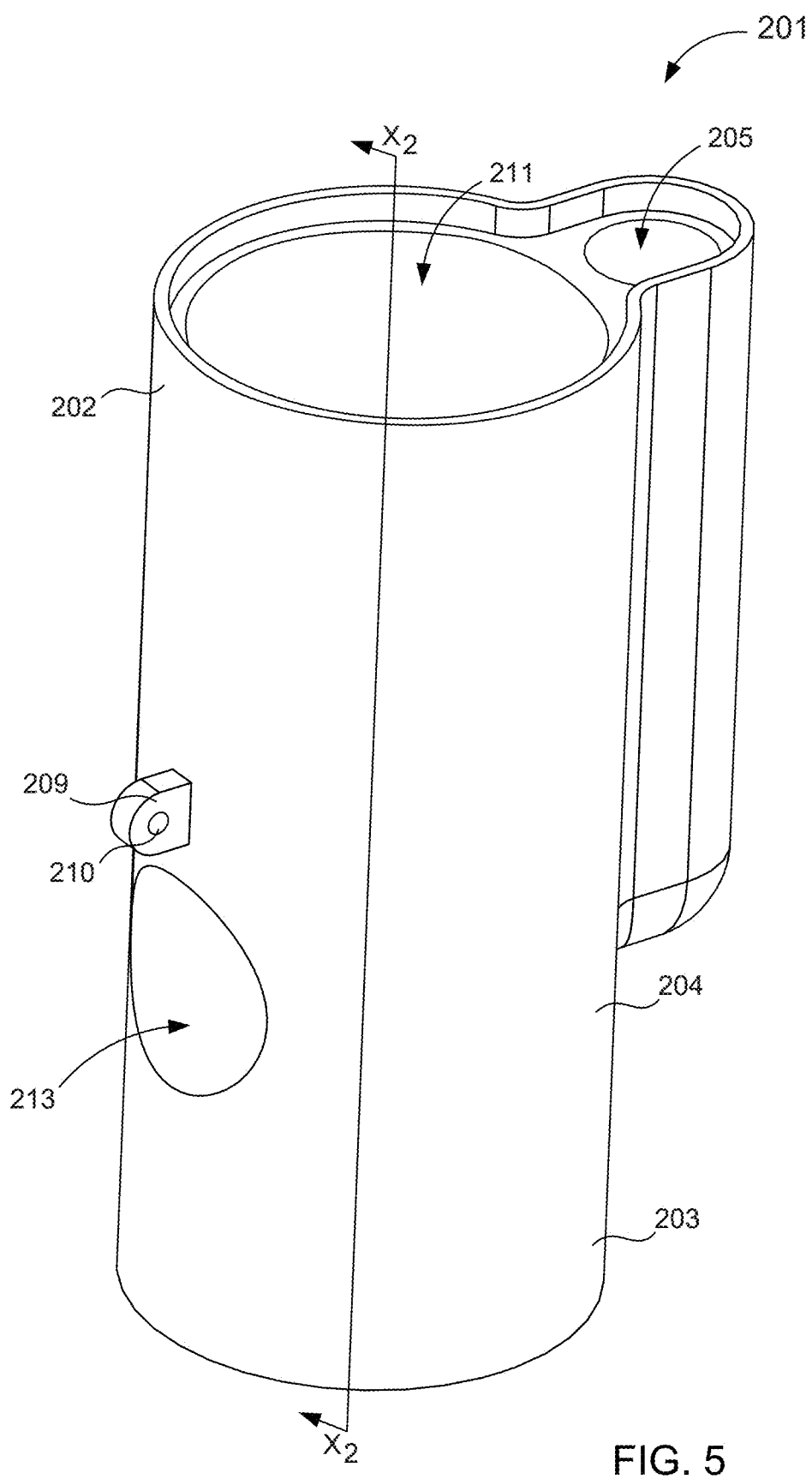
FIG. 5 is a perspective view of a housing included in the bodily-fluid transfer device illustrated in FIG. 2.
Figure 6:
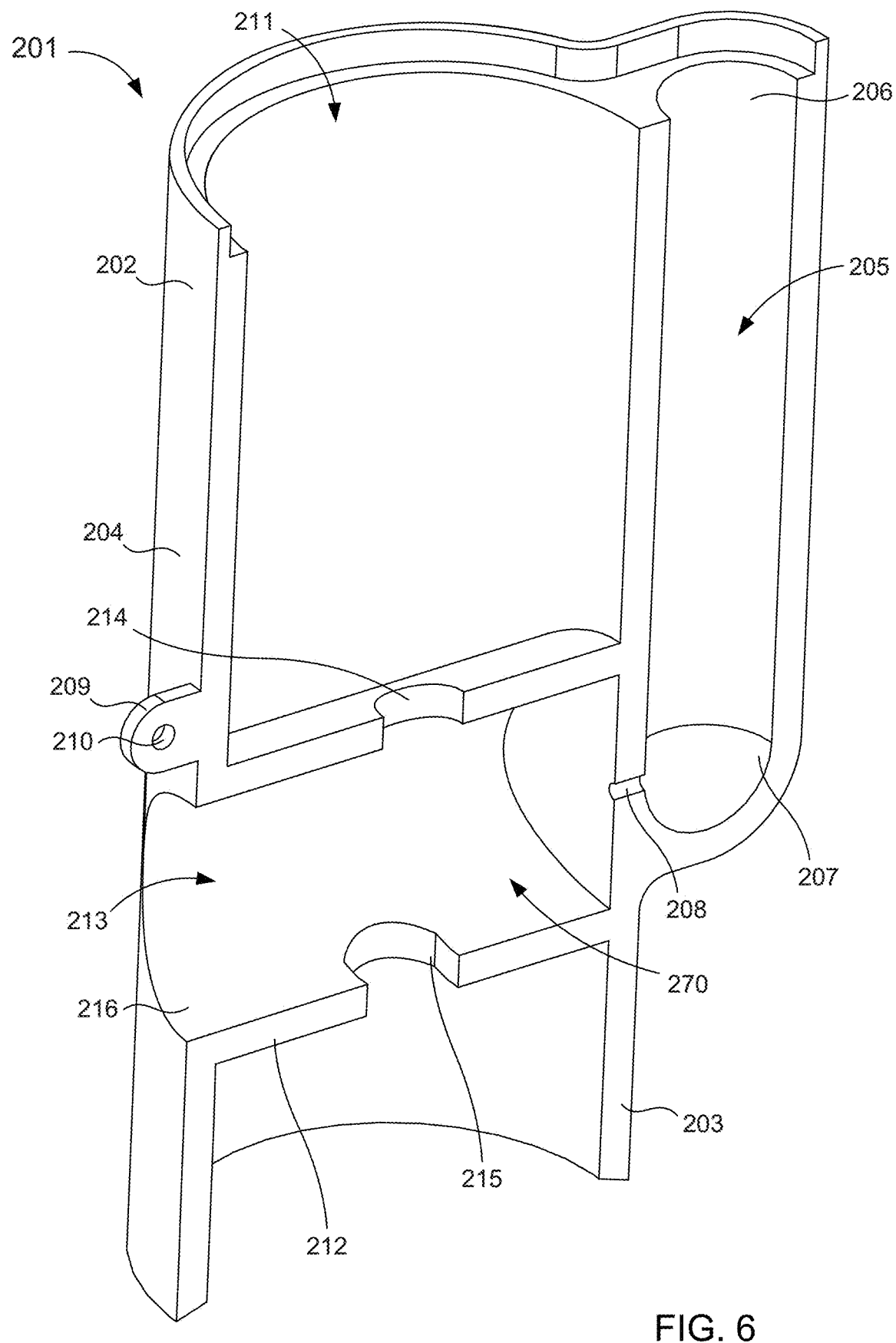
FIG. 6 is a cross-sectional view of the housing illustrated in FIG. 5 taken along the line $X_2$-$X_2$.

As shown in FIG. 5, the walls 204 include a pivot protrusion 209 configured to extend substantially perpendicularly from an outer surface of the walls 204. The pivot protrusion 209 defines an aperture 210 and is configured to receive a portion of the actuator 240 to pivotally couple the actuator 240 to the housing 201. As shown in FIG. 6, the walls 204 define an inner volume 211 and a bypass chamber 205. The bypass chamber 205 includes a first end portion 206 and a second end portion 207. More specifically, the first end portion 206 is disposed at the proximal end portion 202 of the housing 201 and is substantially open such that a bodily-fluid can flow through the first end portion 206 and into the bypass chamber 205. The second end portion 207 defines a lumen 208 configured to place the bypass chamber 205 in fluid communication with a volume of the housing 201 substantially outside of the bypass chamber 205.

The inner walls 212 extend from an inner surface of the walls 204 of the housing 201 to substantially traverse a portion of the inner volume 211. More specifically, the inner walls 212 are substantially annular and define a plunger volume 213 therebetween. The inner walls 212 also define a first opening 214 and a second opening 215. The first opening 214 and the second opening 215 are configured to receive a portion of the diverter 220, such that the portion of the diverter 220 can extend substantially continuously from the proximal end portion 202 of the housing 201 to the distal end portion 203 of the housing 201. In this manner, the portion of the diverter 220 can transfer a bodily-fluid through the housing 201 to an external reservoir while fluidically isolating the bodily-fluid from a volume substantially outside the portion of the diverter 220, as further described herein.

As shown in FIGS. 5 and 6, the plunger volume 213 is configured to extend through a portion of the walls 204 of the housing 201 such that the plunger volume 213 is open to a volume substantially outside of the housing 201. Similarly stated, the walls 204 define an opening 216 configured to be disposed relative to the inner watts 212 to substantially align the opening 216 with a first end of the plunger volume 213. The arrangement of the inner walls 212 relative to the housing 201 is such that the opening 216 and the plunger volume 213 are defined in a distal position relative to the pivot protrusion 209, as further described herein. In addition, the inner walls 212 are configured such that a second end of the plunger volume 213, opposite the first end, is in fluid communication with the lumen 208 of the bypass chamber 205. Thus, at least a portion of the plunger volume 213 and at least a portion of the bypass chamber 205 can define a fluid reservoir 270 configured to receive a flow of bodily-fluid, as described in further detail herein.

Figure 7:
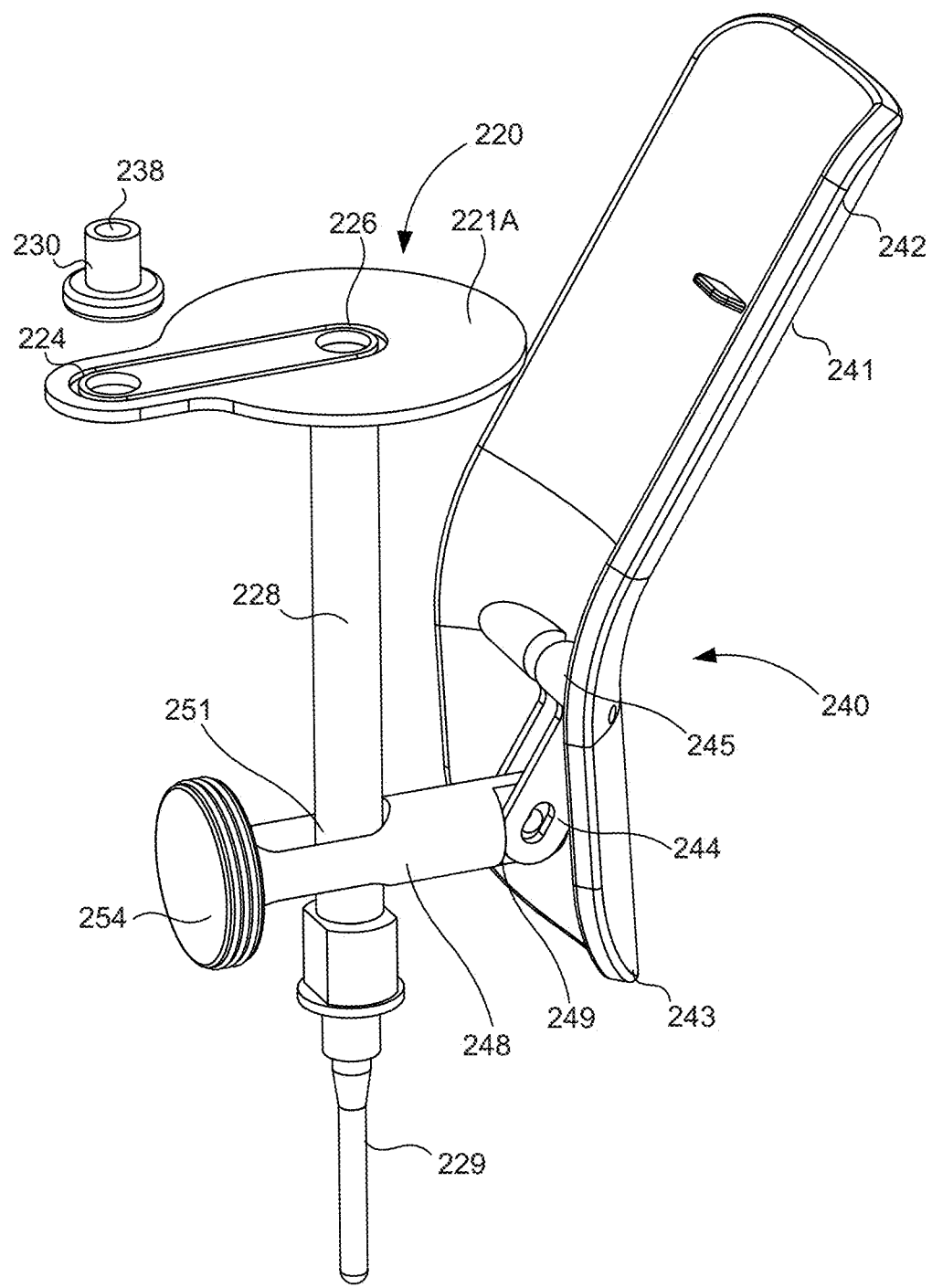
FIG. 7 is a perspective view of a diverter and an actuator included in the bodily-fluid transfer device of FIG. 2.

Referring to FIG. 7, the diverter 220 includes a diverter plate 221A, a transfer tube 228, the outlet adapter 229, and a flow control mechanism 230 (also referred to herein as "inlet port"). The diverter plate 221A is configured to engage a surface of the proximal end portion 202 of the housing 201 to retain the diverter plate 221A relative to the housing 201. For example, in some embodiments, the proximal end portion 202 of the housing 201 can include a flange configured to receive a portion of the diverter plate 221A. In some embodiments, the diverter plate 221A can form a friction fit with an inner surface of the walls 204 of the housing 201, thereby coupling the diverter plate 221A to the housing 201. In such embodiments, at least a portion of the diverter plate 221A can be formed from a relatively flexible material such as a rubber or silicone. In this manner, the portion of the diverter plate 221A can be configured to form a substantially fluid tight seal with the inner surface of the walls 204. In other embodiments, the diverter plate 221A can be coupled to the housing 201 via an adhesive. In such embodiments, the adhesive can be configured to form a substantially fluid tight or hermetic seal.

The diverter plate 221A defines a first port 224 and a second port 226. With the diverter plate 221A disposed within the housing 201 as described above, the first port 224 is in fluid communication with the bypass chamber 205 of the housing 201. Similarly, the second port 226 is in fluid communication with the outlet adapter 229 via the transfer tube 228. Expanding further, a first end of the transfer tube 228 is physically and fluidically coupled to the second port 226 of the diverter plate 221A and a second end of the transfer tube 228 is physically and fluidically coupled to the outlet adapter 229, thereby defining a fluid flow path between the second port 226 and the outlet adapter 229. In this manner, the transfer tube 228 is configured to extend from the proximal end portion 202 of the housing 201 to the distal end portion 203 of the housing 201 via the first opening 214 and the second opening 215 defined by the inner walls 212. Moreover, with a portion of the outlet adapter 229 disposed within the container shroud 218 (as described above), the transfer tube 228 can be configured to transfer a bodily-fluid from the flow control mechanism 230 to an external fluid reservoir, when the external fluid reservoir is fluidically coupled to the outlet adapter 229.

The flow control mechanism 230 (e.g., the inlet port) defines a lumen 238 and is movable between a first position and a second position. More specifically, the flow control mechanism 230 is at least partially disposed within a channel 260 defined by the cap 255 (see e.g., FIG. 4). When the flow control mechanism 230 is in the first position, the lumen 238 is substantially aligned with and in fluid communication with the first port 224 defined by the diverter plate 221A. Similarly, when the flow control mechanism 230 is in the second position, the lumen 238 is configured to be substantially aligned with and in fluid communication with the second port 226 defined by the diverter plate 221A. In some embodiments, the flow control mechanism 230 is configured to be manually moved between the first position and the second position via a force applied by a user (e.g., a medical professional). In other embodiments, the flow control mechanism 230 can be moved automatically by a portion of the transfer device 200 (e.g., the actuator 240 or any other suitable component).

As shown in FIG. 7, the actuator 240 includes a lever 241 and a plunger 248. The actuator 240 is configured to be moved between a first configuration and a second configuration. The lever 241 has a proximal end portion 242, a distal end portion 243, a pivot portion 245, and an engagement portion 244. The pivot portion 245 is configured to be pivotally coupled to the pivot protrusion 209 of the housing 201. For example, in some embodiments, a pivot pin (not shown) can be inserted through the pivot portion 245 of the lever 241 and the aperture 210 defined by the pivot protrusion 209. Similarly, the engagement portion 244 of the lever 241 is configured to be movably coupled to an engagement portion 249 of the plunger member 248. In this manner, the lever 241 can be actuated (e.g., pivoted) about the pivot portion 245 to move the plunger 248 between a first position and a second position, as described in further detail herein.

The plunger 248 is disposed within the plunger volume 213 and includes the engagement portion 249 and a seal member 254. More specifically, the plunger 248 can be movably disposed within the plunger volume 213 such that the engagement portion 249 extends through the opening 216 defined by the walls 204. The seal member 254 is disposed within the plunger volume 213 and engages the inner walls 212 to form a substantially fluid tight seal. The plunger 248 also defines a slot 251 configured to receive the transfer tube 228 of the diverter 220. More specifically, the slot 251 enables the plunger 248 to move about the transfer tube 228 when the transfer tube 228 traverses the plunger volume 213 (e.g., passes through the first opening 214 and the second opening 215 defined by the inner walls 212).

In use, a user can engage the transfer device 200 and couple the flow control mechanism 230 to a proximal end portion of a lumen-defining device (not shown) such as, for example, a butterfly needle. With the flow control mechanism 230 coupled to the lumen-defining device, the lumen 238 is placed in fluid communication with the lumen defined by the lumen-defining device. Furthermore, the distal end portion of the lumen-defining device can be disposed within a portion of the body of a patient (e.g., a vein). In this manner, the lumen 238 is placed in fluid communication with the portion of the body.

With the flow control mechanism 230 coupled to the lumen-defining device, a user can place the transfer device 200 in the first configuration by aligning the flow control mechanism 230 with the first port 224 defined by the diverter plate 221A. For example, in some embodiments, the flow control mechanism 230 is moved via manual intervention (e.g., a user slides the flow control mechanism 230 within the channel 260 to the first position). In other embodiments, the flow control mechanism 230 can be stored in the first configuration. In still other embodiments, the flow control mechanism 230 can be placed in the first configuration via the actuator 240 (e.g., a user engaging the actuator 240 can urge the flow control mechanism 230 to move to the first configuration).

Figure 8:
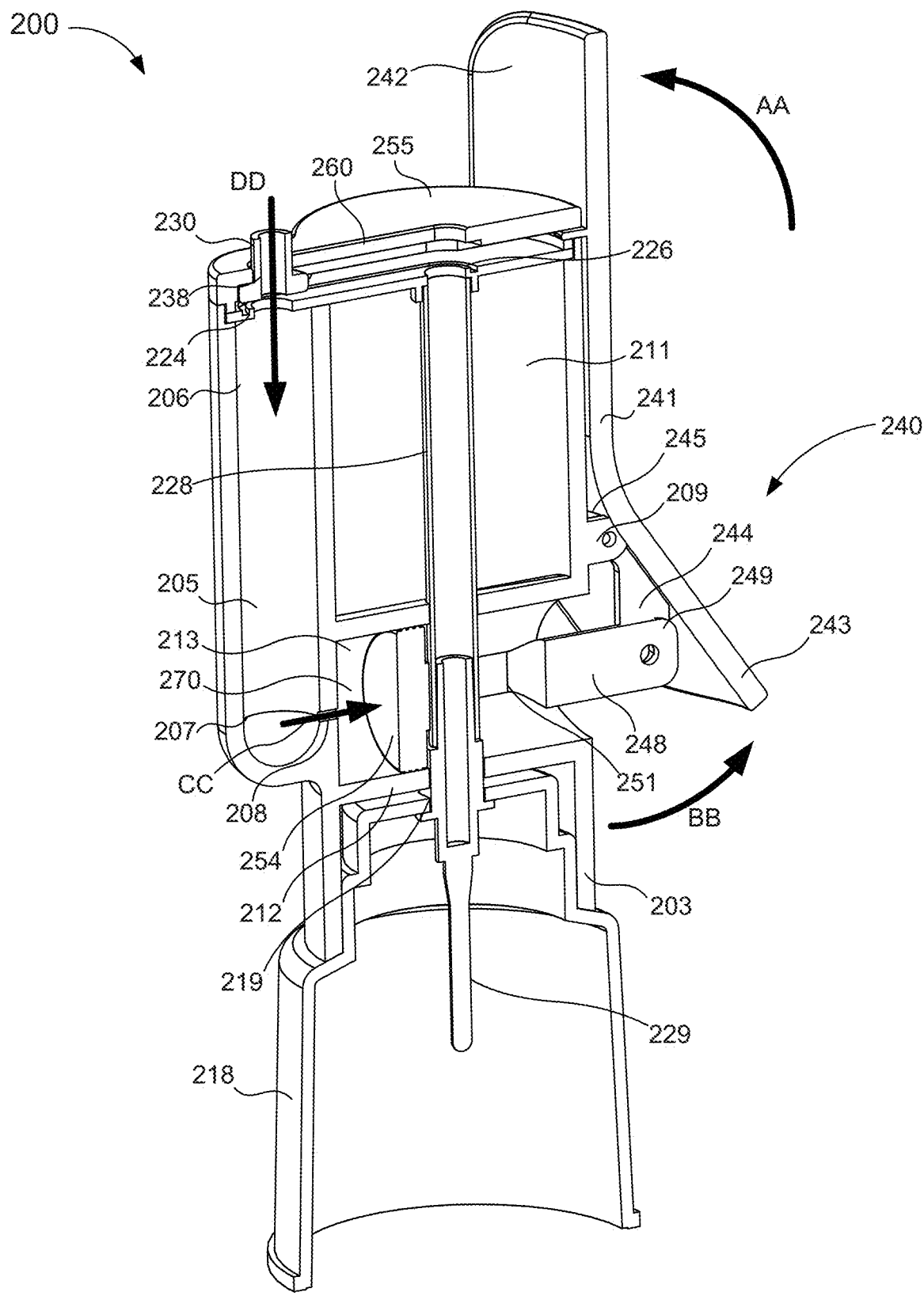
FIG. 8 is a cross-sectional view of the bodily-fluid transfer device of FIG. 2 taken along the line $X_1$-$X_1$, in a second configuration.

As shown in FIG. 8, the lumen 238 is placed in fluid communication with the first port 224 when the flow control mechanism 230 is in the first configuration. In this manner, the user can apply an activation force to the lever 241, thereby moving at least a portion of the actuator mechanism 240 towards the second configuration, as shown by the arrow AA in FIG. 8. More specifically, the user can engage the housing 201 and the lever 241 and exert a squeezing force, thereby moving the proximal end portion 242 of the lever in the direction of the arrow AA. The squeezing force on the proximal end portion 242 urges the lever 241 to pivot about the pivot protrusion 209 of the housing 201 and the pivot portion 245 of the lever 241 such that the distal end portion 243 moves in the direction of the arrow BB. Similarly stated, the user can pivot the lever 241 relative to the housing 201 such that the proximal end portion 242 is moved towards the housing 201 and the distal end portion 243 is moved away from the housing 201.

With the engagement portion 249 of the plunger 248 coupled to the engagement portion 244 of the lever 241, the movement of the distal end portion 243 of the lever 241 in the direction of the arrow BB urges the plunger 248 to move in the direction of the arrow CC. More specifically, the arrangement of the plunger 248, the lever 241, and the inner walls 212 is such that the pivoting motion of the distal end portion 243 of the lever 241 urges the plunger 248 to move in a translational motion within the plunger volume 213 defined by the inner walls 212. In this manner, the plunger 248 is moved away from the bypass chamber 205 such that a volume of the fluid reservoir 270 is increased, thereby producing a negative pressure within the fluid reservoir 270.

As shown by the arrow DD in FIG. 8, the lumen 238 of the flow control mechanism 230 and the first port 224 define a first fluid flow path that places the first end portion 206 of bypass chamber 205 in fluid communication with the flow control mechanism 230. Furthermore, with the flow control mechanism 230 coupled to the lumen-defining device, the fluid reservoir 270 is placed in fluid communication with the portion of the patient (e.g., the vein). In this manner, the negative pressure within the fluid reservoir 270 produced by the movement of the plunger 248 introduces a suction force within the portion of the patient. Thus, a bodily-fluid is drawn through the first end portion 206 of the bypass chamber 205 and into the fluid reservoir 270. In some embodiments, the bodily-fluid can contain undesirable microbes such as, for example, dermally-residing microbes.

In some embodiments, the magnitude of the suction force can be modulated by increasing or decreasing the amount of activation force (e.g., squeezing force) applied to the actuation mechanism 240. For example, in some embodiments, it can be desirable to limit the amount of suction force introduced to a vein. In such embodiments, the user can reduce the amount of force applied to the actuator 240. In this manner, the rate of change (e.g., increase) in the volume of the fluid reservoir 270 can be sufficiently slow to allow time for the negative pressure differential between the vein and the fluid reservoir 270 to come to equilibrium before further increasing the volume of the fluid reservoir 270. Thus, the magnitude of the suction three can be modulated.

With the desired amount (e.g., a predetermined amount) of bodily-fluid transferred to the fluid reservoir 270, the actuator 240 can be moved from the second configuration to a third configuration by reducing or removing the activation force on the proximal end portion 242 of the lever 241. For example, in some embodiments, the actuator 240 can include a spring (not shown) configured to exert a force to move the lever 241 toward the first position relative to the housing 201, thereby placing the transfer device 200 in the third configuration. In other embodiments, the user can apply a squeezing force to the distal end portion 243 of the lever 241 such that the lever 241 pivots about the pivot portion 245. In this manner, the proximal end portion 242 of the lever 241 is configured to move substantially away from the housing 201 as indicated by the arrow EE in FIG. 9. In addition, the distal end portion 243 of the lever is configured to move substantially toward the housing 201 as indicated by the arrow FF in FIG. 9.

The movement of the distal end portion 243 of the lever 241 can be such that the plunger 248 moves within the plunger volume 213 toward the bypass chamber 205 to reduce the negative pressure within the fluid reservoir 270, as described above. With the pressure equalized in the fluid reservoir 270, the flow control mechanism 230 can be moved in the direction of the arrow GG in FIG. 9 to place the lumen 238 in fluid communication with the second port 226 defined by the diverter plate 221A. Similarly stated, the flow control mechanism 230 is moved within the channel 260 of the cap 255 to align the flow control mechanism 230 with the second port 226. The alignment of the flow control mechanism 230 with the second port 226 is such that the portion of the patient (e.g., the vein) is placed in fluid communication with the outlet adapter 229 via the transfer tube 228.

With the flow control mechanism 230 aligned with the second port 226, the outlet adapter 229 can be coupled to an external fluid reservoir (not shown). Expanding further, the external fluid reservoir can be inserted into the container shroud 218 such that a portion of the outlet adapter 229 is disposed within the external fluid reservoir. For example, in some embodiments, the external fluid reservoir can be a BacT/ALERT® SN or a BacT/ALERT® FA, manufactured by BIOMERIEUX, INC. In such embodiments, the outlet adapter 229 can include a piercing member (not shown) such as a needle, configured to pierce a septum or membrane included in the fluid reservoir.

Figure 9:
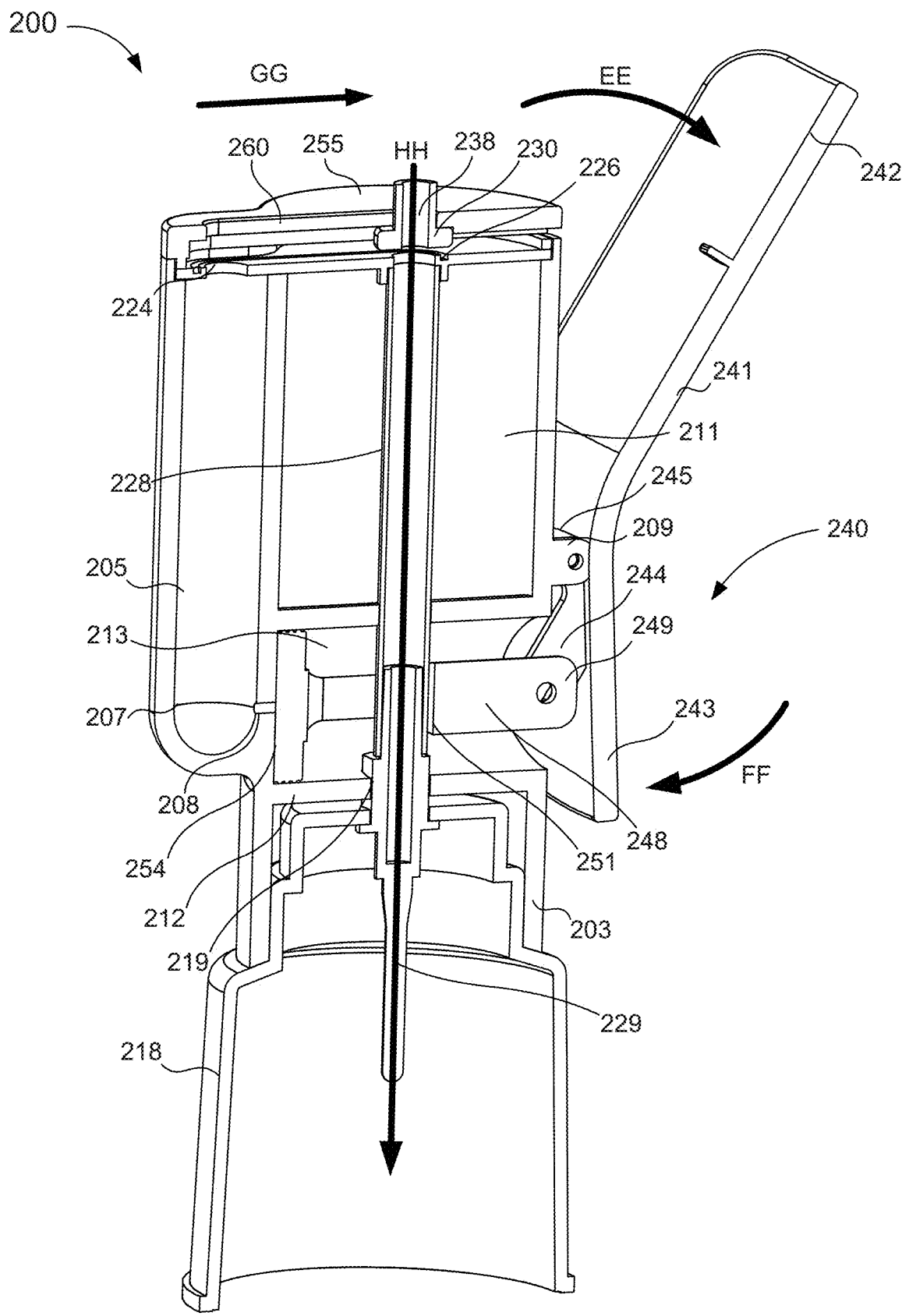
FIG. 9 is a cross-sectional view of the bodily-fluid transfer device of FIG. 2 taken along the line $X_1$-$X_1$, in a third configuration.

As shown by the arrow HH in FIG. 9, the lumen 238 of the flow control mechanism 230, the second port 226, the transfer tube 228, and the outlet adapter 229 define a fluid flow path such that the external reservoir (not shown in FIG. 9) is in fluid communication with the flow control mechanism 230 and, therefore, the portion of the patient (e.g., the vein). Furthermore, the external reservoir can be configured to define a negative pressure (e.g., the known external reservoirs referred to herein are vessels defining a negative pressure). The negative pressure within the external reservoir is such that the negative pressure differential between the external reservoir and the portion of the body of the patient introduces a suction force within the portion of the patient. Therefore, a desired amount of bodily-fluid is drawn into the external reservoir and is fluidically isolated from the first, predetermined amount of bodily-fluid contained within the fluid reservoir 270.

In this manner, the bodily-fluid contained in the external reservoir is substantially free from microbes generally found outside of the portion of the patient (e.g., dermally residing microbes, microbes within a lumen defined by the transfer device 200, microbes within the lumen defined by the lumen defining device, and/or any other undesirable microbe). With the desired amount of bodily-fluid contained in the external fluid reservoir, the user can remove the external fluid reservoir from the transfer device 200 and dispose of the transfer device 200 or utilize the diversion sample contained within the fluid reservoir 270 for other types of testing and/or related medical or non-medical purposes.

Figure 10:
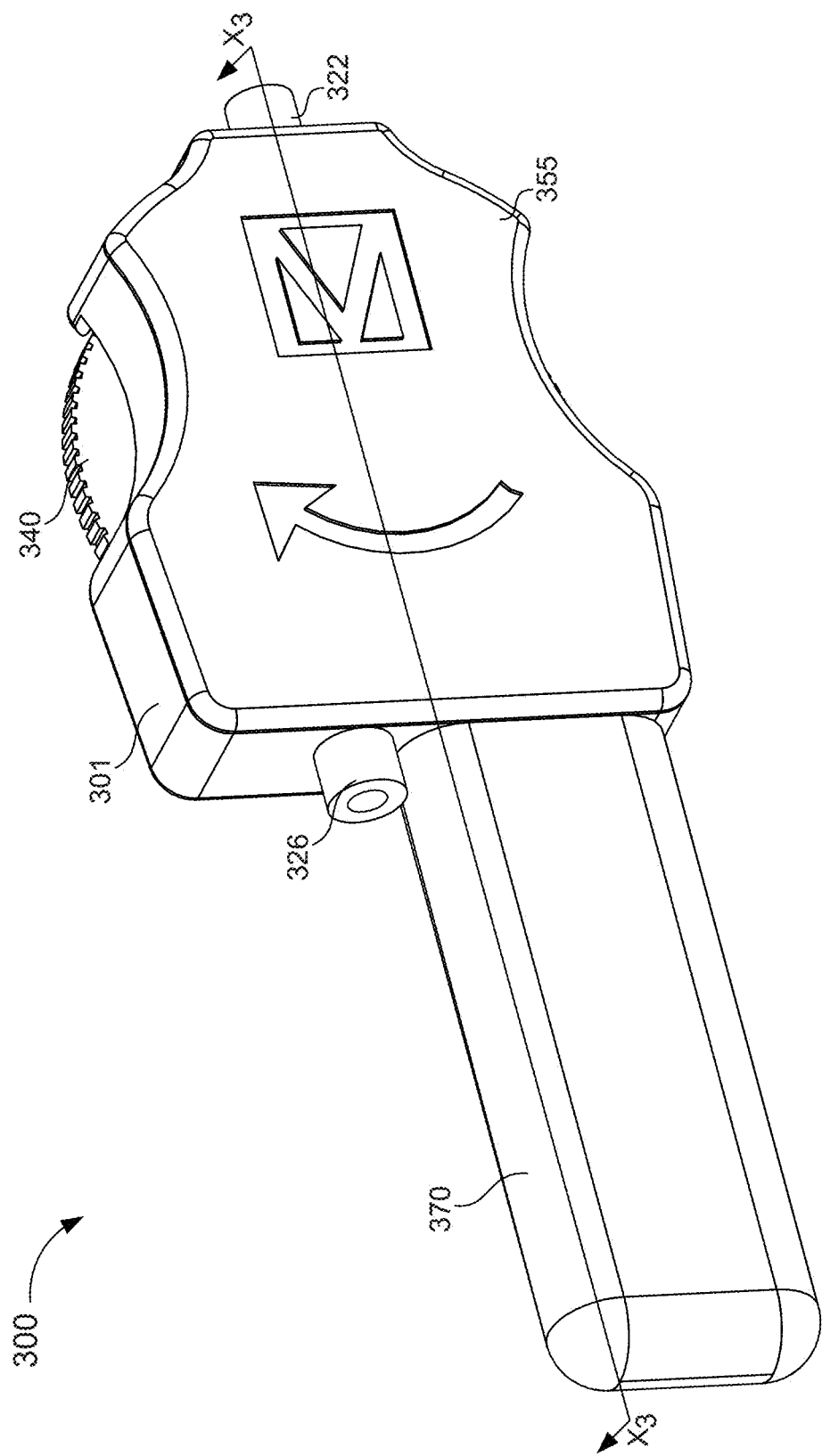
FIG. 10 is a perspective view of the bodily-fluid transfer device according to an embodiment.
Figure 11:
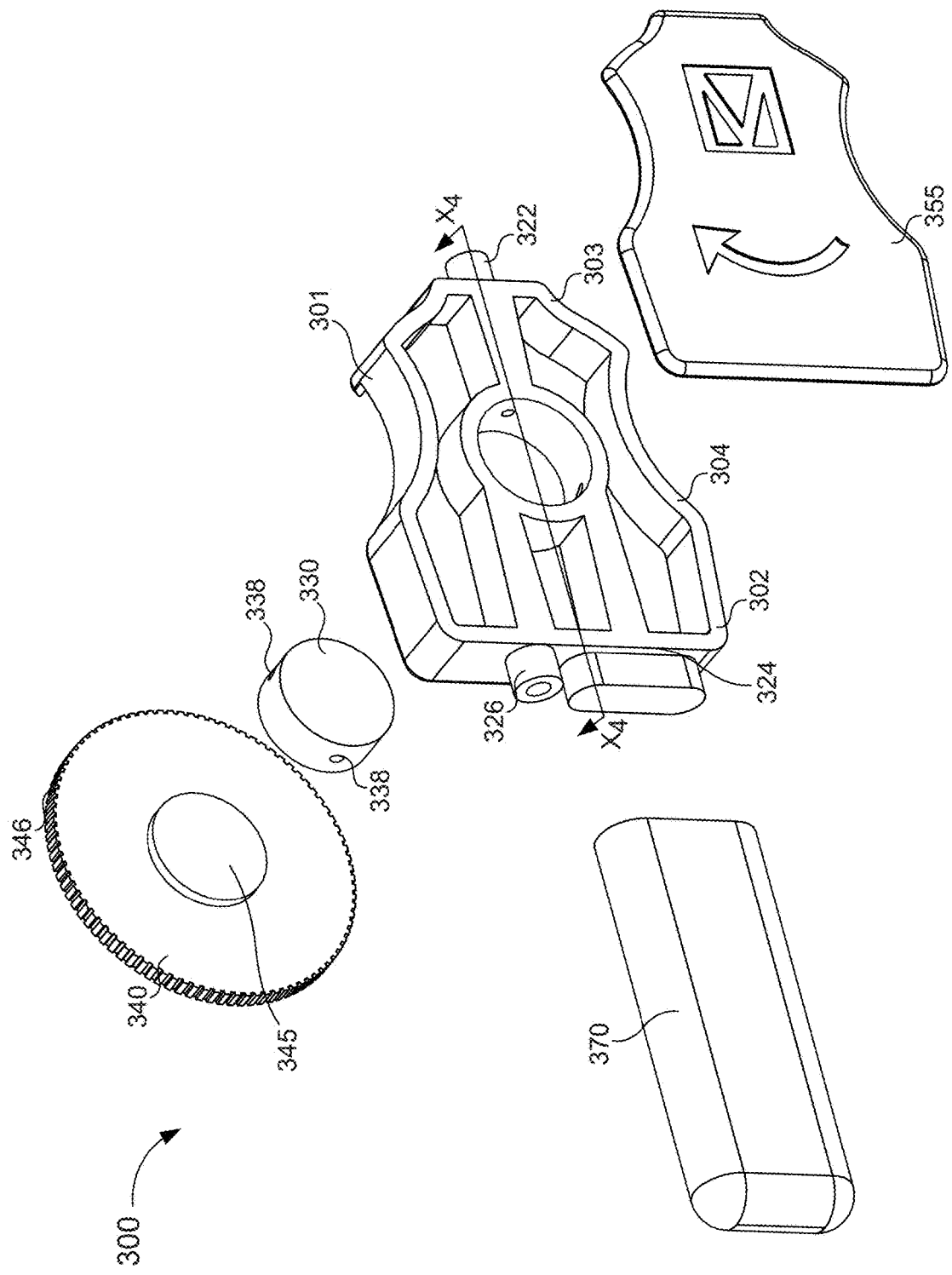
FIG. 11 is an exploded view of the bodily-fluid transfer device of FIG. 10.

While the transfer device 200 is shown and described in FIGS. 2-9 as disposing the diverter 220 within the housing 201, in some embodiments, a transfer device can include a diverter and housing that are monolithically formed. For example, FIGS. 10-15 illustrate a transfer device 300 according to an embodiment. As shown in FIGS. 10 and 11, the transfer device 300 includes a housing 301, having a diverter 320 and defining a fluid reservoir 370, a flow control mechanism 330, and an actuator 340.

The housing 301 includes a proximal end portion 302, a distal end portion 303, and a set of walls 304. More particularly, the housing 301 includes a recessed surface 319 from which the walls 304 extend. Furthermore, at least a portion of the recessed surface 319 is configured to be a flat surface from which the diverter 320 can extend. Similarly stated, the diverter 320 is a set of walls configured to extend perpendicularly from the recessed surface 319. In this manner, the diverter 320 can receive at least a portion of the flow control mechanism 330, as described in further detail herein. While shown and described as extending perpendicularly from the recessed surface 319, in other embodiments, the diverter 320 can extend from the recessed surface 319 at any suitable angular orientation.

Figure 12:
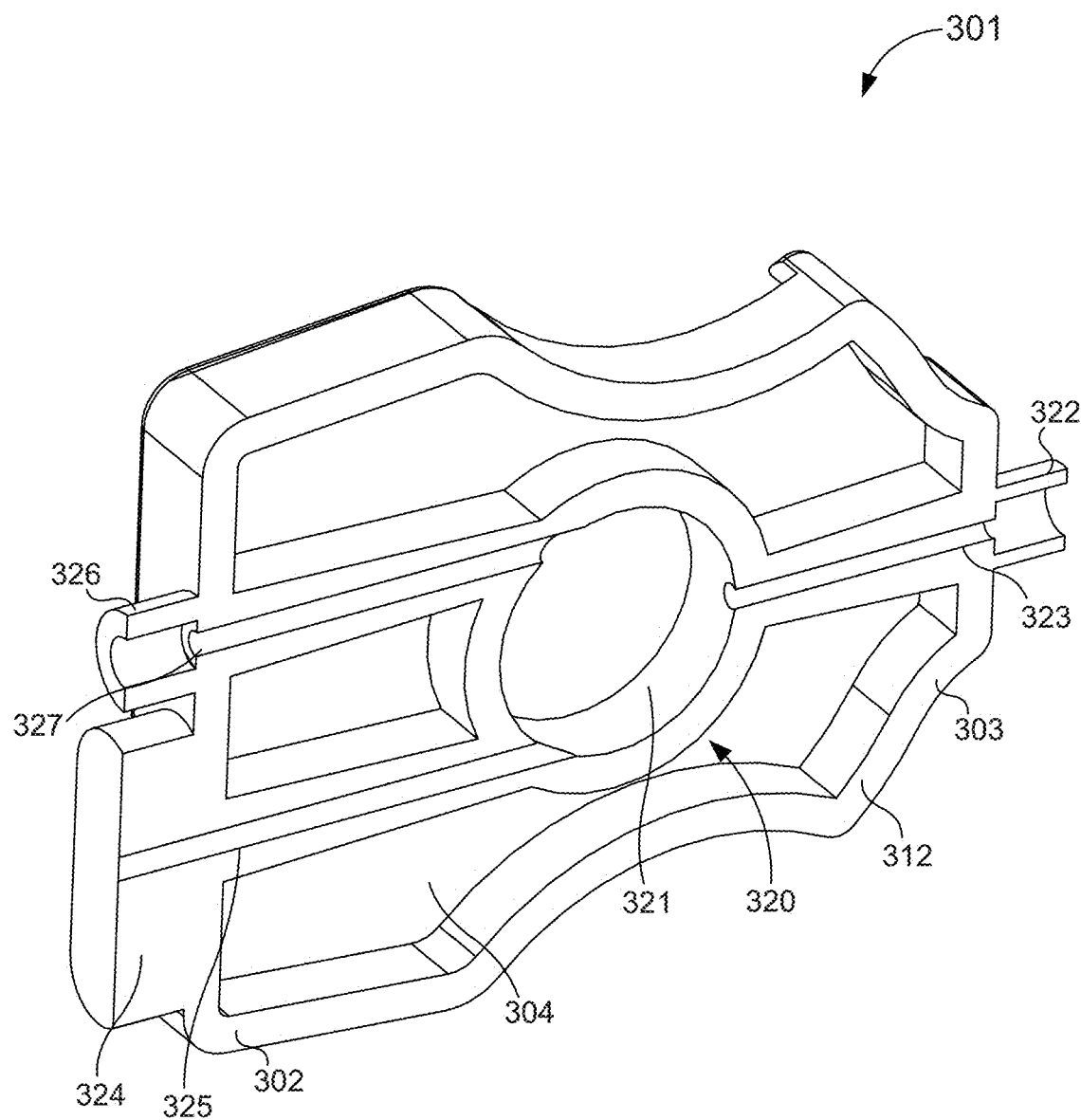
FIG. 12 is a cross-sectional view of a housing included in the bodily-fluid transfer device of FIG. 10 taken along the line $X_4$-$X_4$ in FIG. 11.

As shown in FIG. 12, the diverter 320 includes an inlet port 322, a first outlet port 324, and a second outlet port 326, and defines and inner volume 321. The inner volume 321 is configured to extend through the recessed surface 319 such that the inner volume 321 is substantially open. Similarly stated, the diverter 320 is configured such that a set of walls that define the inner volume 321 are substantially cylindrical and define an open space therebetween (e.g., the inner volume 321). The inner volume 321 is configured to receive at least a portion of the flow control mechanism 330, as further described herein. The inlet port 322 of the diverter 320 defines an inlet lumen 323. The inlet lumen 323 is configured to be in fluid communication with the inner volume 321. Similarly stated, the inlet lumen 323 of the inlet port 322 extends through the wall defining the inner volume 321 of the diverter 320.

The inlet port 322 is further configured to be fluidically coupled to a medical device (not shown) defining a fluid flow pathway fir withdrawing and/or conveying the bodily-fluid from a patient to the transfer device 300. For example, the inlet port 322 can be fluidically coupled to a needle or other lumen-defining device (e.g., flexible sterile tubing) as described above. In this manner, when the lumen-defining device is disposed within a portion of a body of the patient (e.g., within a vein of the patient), the inner volume 321 of the diverter 320 is placed in fluid communication with the portion of the body of the patient.

The first outlet port 324 of the diverter 320 defines a first outlet lumen 325. The first outlet lumen 325 is in fluid communication with the inner volume 321 of the diverter 320 and the fluid reservoir 370 (described above). Similarly stated, the first outlet lumen 325 is configured to extend through the wall defining the inner volume 321, thereby placing the fluid reservoir 370 in fluid communication with the inner volume 321. The second outlet port 326 of the diverter 320 defines a second outlet lumen 327 and is configured to be coupled to an external fluid reservoir. In this manner, the second outlet lumen 327 can extend through the wall defining the inner volume 321 to be in fluid communication with the inner volume 321. Moreover, the second outlet port 326 can be fluidically coupled to the external reservoir to place the external fluid reservoir in fluid communication with the inner volume 321 via the second outlet lumen 327, as described in further detail herein.

Referring back to FIG. 11, the actuator mechanism 340 includes an engagement portion 345 and an activation portion 346. The actuator mechanism 340 can be coupled to the housing 301 in any suitable manner. For example, in some embodiments, a portion of the actuator mechanism 340 can be disposed within the inner volume 321. In some embodiments, the walls 304 can include a feature e.g., a tab, a lock, and/or the like) configured to selectively retain the actuator mechanism 340 in contact with the housing 301. The activation portion 346 is configured to contact, mate, or otherwise engage the flow control mechanism 330. In this manner, the engagement portion 345 can be engaged by a user to rotate the actuator mechanism 340 relative to the housing 301 to move the transfer device 300 between a first configuration, a second configuration, and a third configuration, as described in further detail herein.

Figure 13:
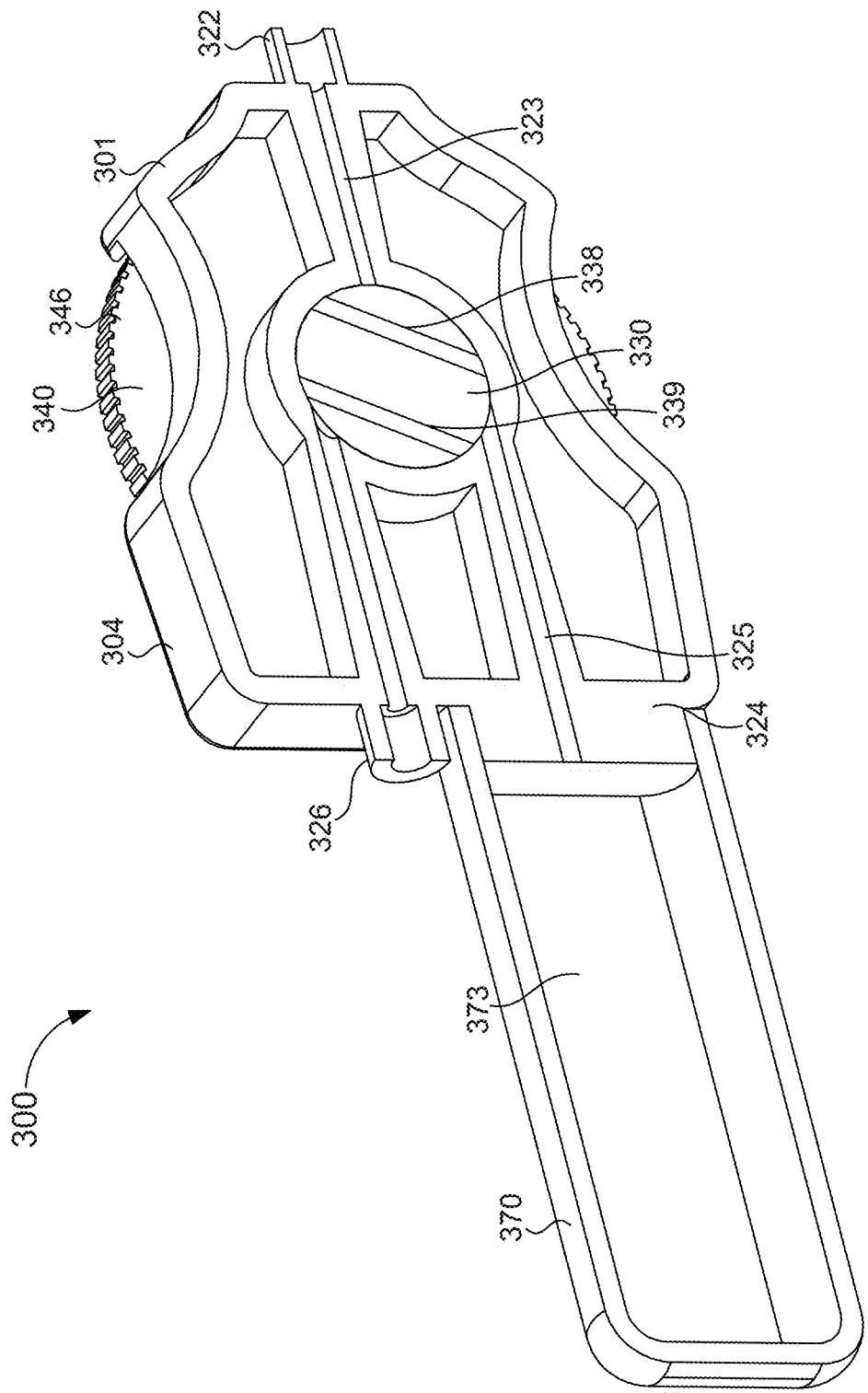
FIGS. 13-15 are cross-sectional views of the bodily-fluid transfer device taken along the line $X_4$-$X_4$ in FIG. 11, in a first, second, and third configuration, respectively.

As shown in FIG. 13, the flow control mechanism 330 defines a first lumen 338 and a second lumen 339 and is disposed within the inner volume 321 defined by the diverter 320. In this manner, the flow control mechanism 330 defines a circular cross-sectional shape such that when the flow control mechanism 330 is disposed within the inner volume 321, a portion of the flow control mechanism 330 forms a friction fit with the walls of the diverter 320 defining the inner volume 321. For example, in some embodiments, the flow control mechanism 330 is formed from silicone and has a diameter larger than the diameter of the walls defining the inner volume 321. As such, the diameter of the flow control mechanism 330 is reduced when the flow control mechanism 330 is disposed within the inner volume 321. Thus, the outer surface of the flow control mechanism 330 forms a friction fit with the inner surface of the walls defining the inner volume 321. In other embodiments, the flow control mechanism 330 can be any suitable elastomer configured to deform when disposed within the inner volume 321 of the diverter 320.

The flow control mechanism 330 can be coupled to and/or can otherwise engage the actuator 340. For example, in some embodiments, the actuator 340 can be coupled to the flow control mechanism 330 via a mechanical fastener and/or adhesive. In other embodiments, the actuator 340 and the flow control mechanism 330 can be coupled in any suitable manner such that the flow control mechanism 330 moves concurrently with the actuator 340 when the actuator 340 is rotated relative to the housing 301. In this manner, the flow control mechanism 330 can be moved relative to the diverter 320 to place the first lumen 338 or the second lumen 339 in fluid communication with the inlet port 322, the first outlet port 324, and/or the second outlet port 326, as described in further detail herein.

As shown in FIG. 13, the transfer device 300 can be stored in the first configuration in which the flow control mechanism 330 fluidically isolates the inlet port 322 from the first outlet port 324 and the second outlet port 326. Expanding further, the flow control mechanism 330 can be disposed within the inner volume 321 of the diverter 320 such that the first lumen 338 and the second lumen 339 are fluidically isolated from the inlet lumen 323, the first outlet lumen 325, and the second outlet lumen 327. In such embodiments, the friction fit defined by the flow control mechanism 330 and the walls of the diverter 320 defining the inner volume 321 maintain the flow control mechanism 330 in the first configuration until, for example, user intervention moves the actuator 340, thereby moving the flow control mechanism 330 to the second configuration.

In use, a user can manipulate the transfer device 300 to couple the inlet port 322 to a proximal end portion of a lumen-defining device (not shown) such as, for example, a butterfly needle and/or the like. Furthermore, the distal end portion of the lumen-defining device can be disposed within a portion of the body of a patient (e.g., a vein) to place the inlet lumen 323 in fluid communication with the portion of the body of the patient. In a similar manner, the second outlet port 326 can be coupled to an external fluid reservoir (not shown). The external fluid reservoir can be any suitable reservoir. For example, in some embodiments, the external fluid reservoir can be a BacT/ALERT® SN or a BacT/ALERT® FA, manufactured by BIOMERIEUX, INC.

Figure 14:
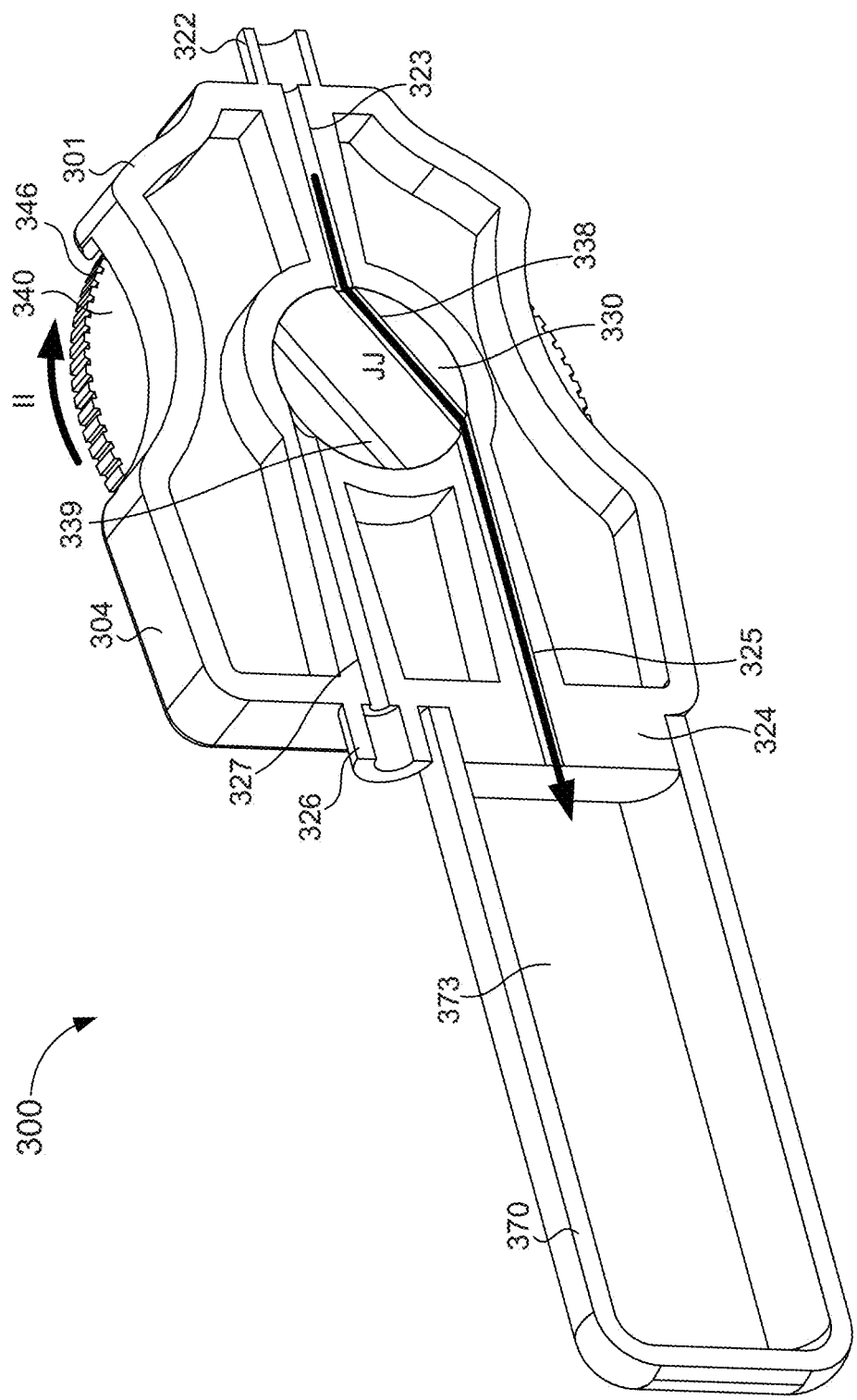

With the inlet port 322 coupled to the lumen-defining device and the second outlet port 326 coupled to the external fluid reservoir, a user can begin the transfer of a bodily-fluid by applying an activation force to the engagement portion 344 of the actuator 340, thereby moving the actuator 340 to a second position, as shown by the arrow II in FIG. 14. The movement of the actuator 340 is such that the flow control member 340 is urged to move in the direction of the arrow II, thereby placing the transfer device 300 in the second configuration. In addition, the fluid reservoir 370 can be configured such that a negative pressure exists within an inner volume 373 such as, for example, an evacuated sample tube (e.g., BD Vacutainer®). Therefore, when the flow control mechanism 330 is placed in its second configuration, a negative pressure differential introduces a suction force within the first lumen 338 of the flow control mechanism 330, and the inlet lumen 323 and the first outlet lumen 325 of the diverter 320.

As shown by the arrow JJ, the inlet lumen 323 of the inlet port 322, the first lumen 338 of the flow control mechanism 330, and the first outlet lumen 325 of the first outlet port 324 define a first fluid flow path that places the inner volume 373 defined by the fluid reservoir 370 in fluid communication with the inlet port 322. Furthermore, with the inlet port 322 coupled to the lumen-defining device, the first fluid flow path places the fluid reservoir 370 in fluid communication with the portion of the patient (e.g., the vein) and at least a portion of the suction force (e.g., applied by the negative pressure differential, as described above) is introduced to the portion of the patient. Thus, a bodily-fluid can be drawn into the fluid reservoir 370. In some embodiments, the bodily-fluid can contain undesirable microbes such as, for example, dermally-residing microbes dislodged during the insertion of the lumen-defining device.

In some embodiments, the magnitude of the suction force can be modulated by further moving the actuator 340 in the direction of the arrow II. For example, in some embodiments, it can be desirable to limit the amount of suction force introduced to a vein. In such embodiments, the user can move the actuator 340 and the flow control mechanism 330 (e.g., in the II direction) to constrict or otherwise reduce the size of at least a portion of the first fluid pathway (e.g., an inner diameter) between the inlet lumen 323 and the first lumen 338 and the first outlet lumen 325 and the first lumen 338, thereby reducing the suction force introduced into the vein of the patient.

With the desired amount of bodily-fluid transferred to the fluid reservoir 370, a user can engage the transfer device 300 to move the transfer device 300 from the second configuration to the third configuration, wherein a flow of bodily-fluid is transferred to the external reservoir (e.g., such as those described above). In some embodiments, the desired amount of bodily-fluid transferred to the fluid reservoir 370 is a predetermined amount of fluid. For example, in some embodiments, the transfer device 300 can be configured to transfer bodily-fluid until the pressure within the fluid reservoir 370 is equilibrium with the pressure of the portion of the body in which the lumen-defining device is disposed (e.g., the vein), as described above. In some embodiments, at least a portion of the fluid reservoir 370 can be transparent to allow visualization of the bodily fluid flowing into the fluid reservoir 370. Although not shown, the fluid reservoir 370 can include indicators (e.g., 0.1 mL, 0.5 mL, 1 mL, 2 mL, 3 mL, 4 mL, and/or 5 mL graduation marks) that the user can visualize to determine the volume of bodily-fluid that has been received in the fluid reservoir 370.

Figure 15:
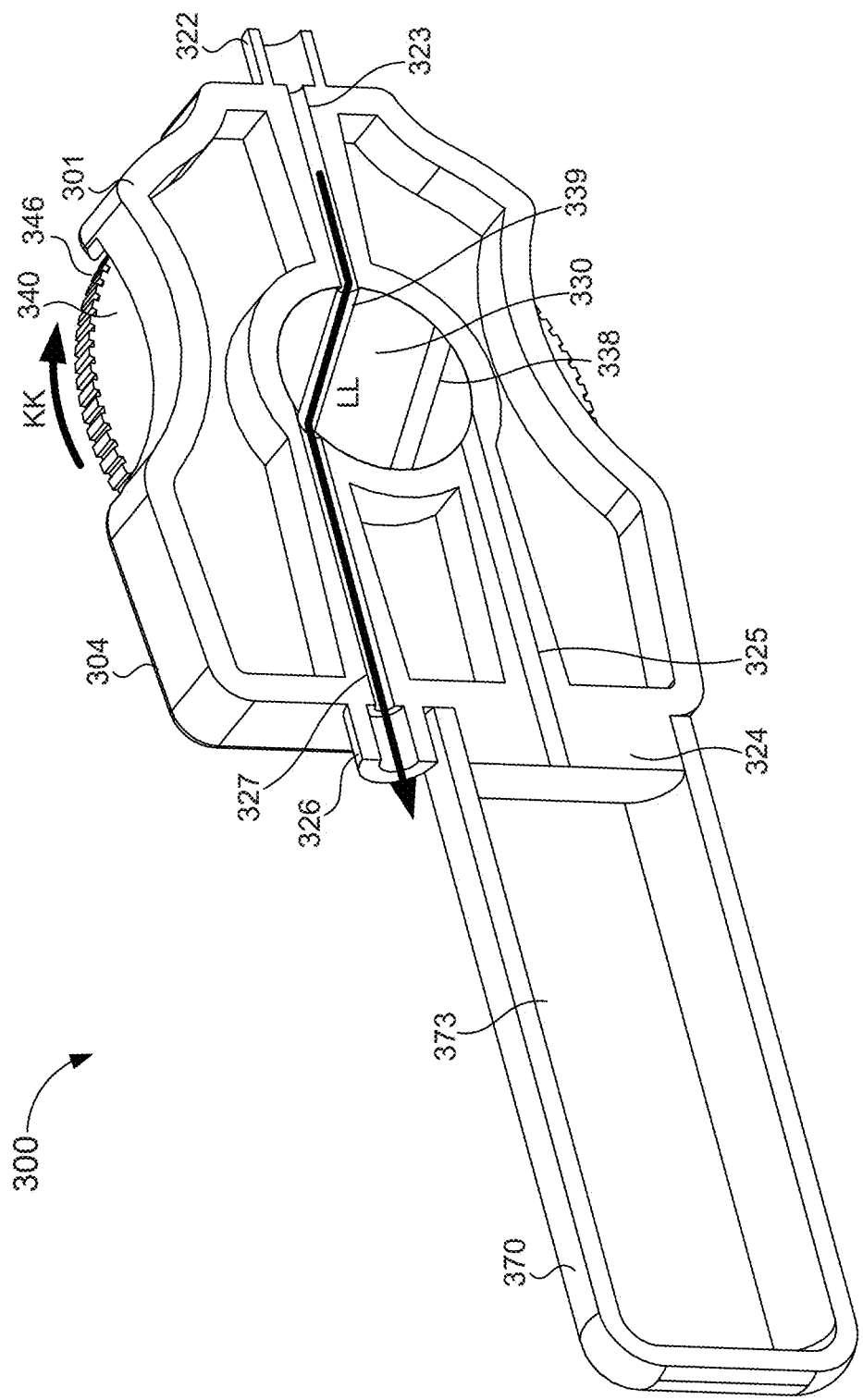

The transfer device 300 can be moved from the second configuration to the third configuration by moving the actuator mechanism 340 in the direction of the arrow KK in FIG. 15. As the actuator mechanism 340 is moved from its second configuration toward its third configuration, the actuator 340 rotates the flow control mechanism 330 toward the third configuration. In this manner, the first lumen 338 is fluidically isolated from the inlet lumen 323 and the first outlet lumen 325, and the second lumen 339 is placed in fluid communication with the inlet lumen 323 defined by the inlet port 322 and the second outlet lumen 327 defined by the second outlet port 326.

As shown by the arrow LL in FIG. 15, the inlet lumen 323 of the inlet port 322, the second lumen 339 of the flow control mechanism 330, and the second outlet lumen 327 of the second outlet port 326 define a second fluid flow path that can place the external reservoir (not shown in FIG. 15) in fluid communication with the inlet port 322 and, therefore, the portion of the patient (e.g., the vein). Furthermore, the external reservoir can be configured to define a negative pressure (e.g., the known external reservoirs referred to herein are vessels defining a negative pressure). The negative pressure within the external reservoir is such that the negative pressure differential between the external reservoir and the portion of the body of the patient introduces a suction force within the portion of the patient. Therefore, a desired amount of bodily-fluid is drawn into the external reservoir and is fluidically isolated from the first, predetermined amount of bodily-fluid contained within the fluid reservoir 370.

The bodily-fluid contained in the external reservoir is substantially free from microbes generally found outside of the portion of the patient (e.g., dermally residing microbes, microbes within a lumen defined by the transfer device 300, microbes within the lumen defined by the lumen defining device, and/or any other undesirable microbe). In some embodiments, with the desired amount of bodily-fluid contained in the external fluid reservoir, the user can further move the actuator 340 in the proximal direction to place the transfer device 300 in a fourth configuration. In such embodiments, the actuator 340 can be moved in the direction of the arrow KK to fluidically isolate the first lumen 338 and the second lumen 339 of the flow control mechanism 330 from the inlet lumen 323, the first outlet lumen 325, and the second outlet lumen 327 of the diverter 320. Thus, the bodily-fluid contained within the fluid reservoir 370 is fluidically isolated from a volume outside the fluid reservoir 370 and the external reservoir can be decoupled from the transfer device 300. In some instances, additional external reservoirs can then be fluidically coupled to the transfer device 300, and the user can rotate the actuator 340 back to the third configuration to establish fluid communication between the patient and the additional external reservoir and/or sample vessel. In some embodiments, the actuator 340 can include a sensible indication (e.g., audible, visual and/or tactile) of which position the transfer device 300 is in. For example, the actuator can include numeric indicators of the position of the transfer device 300.

While various embodiments have been described above, it should be understood that they have been presented by way of example only, and not limitation. Where methods and steps described above indicate certain events occurring in certain order, those of ordinary skill in the art having the benefit of this disclosure would recognize that the ordering of certain steps may be modified and that such modifications are in accordance with the variations of the invention. Additionally, certain of the steps may be performed concurrently in a parallel process when possible, as well as performed sequentially as described above. Additionally, certain steps may be partially completed before proceeding to subsequent steps.

While the lever 241 is described in reference to FIG. 9 as being returned to the first position relative to the housing 201 when the transfer device 200 is moved to the third configuration, in other embodiments, the lever 241 need not be moved from the second position relative to the housing 201. For example, in some embodiments, the pressure differential between the vein and the fluid reservoir 270 can be in equilibrium without substantially reducing the volume of the fluid reservoir 270. Thus, the plunger 248 need not be moved toward the bypass chamber 205 and the lever 241 of the actuator 240 can remain in the second position relative to the housing 201 while a bodily-fluid is transferred to an external reservoir.

While various embodiments have been particularly shown and described, various changes in form and details may be made. For example, while the actuator 340 is shown and described with respect to FIGS. 13-15 as being rotated in a single direction, in other embodiments, an actuator can be rotated in a first direction (e.g., in the direction of the arrow II in FIG. 14) and a second direction, opposite the first. In such embodiments, the rotation in the second direction can be configured to move a transfer device through any number of configurations. In other embodiments, the rotation of the actuator in the second direction can be limited. For example, in some embodiments, the actuator can be limitedly rotated in the second direction to reduce the diameter of a flow path between a flow control mechanism and a lumen such as to reduce a suction force, as described above. In some embodiments, the actuator can include a mechanical stop or lock to fluidically isolate the first volume of bodily fluid received from the patient (i.e., the contaminated sample). Said another way, once the first reservoir is filed with a predetermined volume of bodily fluid and the user has moved the actuator to being drawing additional sample, the actuator cannot be moved back to establish fluid communication the first sample volume.

Although various embodiments have been described as having particular features and/or combinations of components, other embodiments are possible having any combination or sub-combination of any features and/or components from any of the embodiments described herein. For example, while the transfer device 300 is shown and described with respect to FIGS. 13-15 as having a first, second, third and forth configuration, in other embodiments, the transfer devices described herein may have more or fewer configurations.

The specific configurations of the various components can also be varied. For example, the size and specific shape of the various components can be different than the embodiments shown, while still providing the functions as described herein. More specifically, the size and shape of the various components can be specifically selected for a desired rate of bodily-fluid flow into a fluid reservoir.

The invention claimed is:

1. A method for procuring bodily-fluid samples from a patient using a parenteral sampling device, the device including a housing, an actuator coupled to the housing, a pre-sample reservoir collectively defined by the actuator and the housing, and a flow control mechanism, the method comprising:

establishing fluid communication between a patient and the pre-sample reservoir;

withdrawing a first volume of bodily-fluid by moving the actuator relative to the housing from a first position to a second position to create a negative pressure in the pre-sample reservoir;

moving the flow control mechanism from a first configuration to a second configuration, the first configuration operable to allow bodily-fluid to flow through a first flow path from the patient to the pre-sample reservoir, the second configuration operable to allow bodily-fluid to flow through a second flow path from the patient to a sample reservoir, the first fluid flow path at least partially defined by the housing, the second fluid flow path fluidically isolated from the pre-sample reservoir and extending though the housing; and inserting a portion of the sample reservoir into the housing to place the sample reservoir in fluid communication with the second flow path after the flow control mechanism is in the second configuration.

2. The method of claim 1, wherein moving the flow control mechanism from the first configuration to the second configuration includes sliding the flow control mechanism from a first position to a second position.

3. The method of claim 1, wherein moving the actuator from the first position to the second position includes rotating a lever around a pivot point.

4. The method of claim 1, wherein withdrawing the first volume of bodily-fluid includes withdrawing at least a predetermined volume that includes contaminants such that when the flow control mechanism is in the second configuration, the sample reservoir receives, via the second flow path, a flow of bodily-fluid that is substantially free from contaminants.

5. The method of claim 1, wherein the actuator includes a plunger coupled to a lever, moving the actuator from the first position to the second position includes moving the plunger in a linear direction from the first position to the second position in response to a rotation of the lever around a pivot point.

6. The method of claim 1, wherein the parenteral sampling device includes an outlet port configured to be fluidically coupled to the sample reservoir, the flow control mechanism being in fluid communication with the pre-sample reservoir when the flow control mechanism is in the first configuration, the moving of the flow control mechanism from the first configuration to the second configuration is such that (1) the first volume of bodily-fluid is sequestered in the pre-sample reservoir and (2) fluid communication is established between the flow control mechanism and the outlet port.

7. The method of claim 1, wherein the actuator includes a seal member configured to form a substantially fluid tight seal with an inner surface of the pre-sample reservoir, the moving of the actuator from the first position to the second position includes moving the seal member within the pre-sample reservoir to increase a volume of the pre-sample reservoir.

8. The method of claim 7, wherein the increase in volume of the pre-sample reservoir produces the negative pressure within the pre-sample reservoir.

9. A method for procuring bodily-fluid samples from a patient using a parenteral sampling device, the device including a housing, a flow control mechanism movably coupled to the housing, an actuator movably coupled to the housing, and an integrated pre-sample reservoir collectively defined by the actuator and the housing, the method comprising:

inserting a needle into the patient while the flow control mechanism is in a first configuration, the first configuration operable to prevent bodily-fluid from flowing from the patient to the integrated pre-sample reservoir;

moving the flow control mechanism from the first configuration to a second configuration, the second configuration operable to allow bodily-fluid to flow through a first flow path at least partially defined by the housing and the flow control mechanism to the integrated pre-sample reservoir;

moving the actuator from a first position to a second position to create a negative pressure in the pre-sample reservoir;

moving the flow control mechanism from the second configuration to a third configuration after a predetermined volume of bodily-fluid has been received in the pre-sample reservoir, the third configuration operable to allow bodily-fluid to flow through a second flow path defined at least in part by the flow control mechanism and extending through the housing; and inserting a portion of a sample reservoir into the housing to place the sample reservoir in fluid communication with the second flow path after the flow control mechanism is in the third configuration.

10. The method of claim 9, wherein the pre-sample reservoir is sequestered from the second fluid flow path.

11. The method of claim 9, further comprising:
moving the flow control mechanism from the third configuration to a fourth configuration, the fourth configuration operable to prevent bodily-fluid from flowing through the first flow path and the second flow path.

12. The method of claim 9, wherein the parenteral sampling device further includes a lock, the lock configured to prevent the flow control mechanism from being moved back to the second configuration once the flow control mechanism has been moved to the third configuration.

13. The method of claim 9, wherein moving the flow control mechanism from the first configuration to the second configuration includes moving the flow control mechanism in a first direction, the moving of the flow control mechanism from the second configuration to the third configuration includes moving the flow control mechanism in a second direction opposite the first direction.

14. A method for procuring bodily-fluid samples from a patient using a parenteral sampling device, the device including a housing, an actuator movably coupled to the housing, a pre-sample reservoir collectively defined by the actuator and the housing, a flow control mechanism movably coupled to a diverter, the diverter coupled to the housing and having a first port in fluid communication with the pre-sample reservoir and a second port configured to be placed in fluid communication with a sample reservoir, the method comprising:

establishing fluid communication between the patient and the device when the flow control mechanism is in a first position;

exerting a first amount of force on a portion of the actuator to move the flow control mechanism from the first position to a second position to define a first flow path, the first flow path defined at least in part by the first port of the diverter and a portion of the housing;

transferring a first amount of bodily-fluid, via the first flow path and the first port, from the patient to the pre-sample reservoir;

exerting a second amount of force on a portion of the actuator to move the flow control mechanism from the second position to a third position to define a second flow path, the second flow path defined at least in part by the second port of the diverter and extending through the housing; and inserting a portion of the sample reservoir into the housing to place the sample reservoir in fluid communication with the second flow path after the flow control mechanism is in the third position.

15. The method of claim 14, further comprising:
transferring a second amount of bodily fluid to the sample reservoir via the second flow path.

16. The method of claim 14, wherein at least a portion of the actuator is rotated relative to the diverter in response to the exerting of the first amount of force or the second amount of force.

17. The method of claim 14, wherein the flow control mechanism defines a lumen, the lumen defining a portion of the first flow path when the flow control mechanism is in the second position, the lumen defining a portion of the second flow path when the flow control mechanism is in the third position.

18. The method of claim 14, wherein exerting the first amount of force on the actuator includes exerting the first amount of force on a first portion of the actuator and the exerting of the second amount of force on the actuator includes exerting the second amount of force on a second portion of the actuator, the first amount of force and the second amount of force being exerted in the same direction.

19. The method of claim 14, wherein exerting the first amount of force on the actuator includes exerting the first amount of force on the portion of the actuator in a first direction, the exerting of the second amount of force on the portion of the actuator includes exerting the second amount of force in a second direction opposite the first direction.

* * * * *